United States Patent [19]

Ono et al.

[11] Patent Number: 5,026,634
[45] Date of Patent: Jun. 25, 1991

[54] COLOR LIGHT-SENSITIVE MATERIAL

[75] Inventors: Michio Ono; Hiroyuki Hirai; Nobutaka Ohki; Kouichi Hanaki; Koki Nakamura, all of Kanagawa, Japan

[73] Assignee: Fuji Photo Film Co., Ltd., Kanagawa, Japan

[21] Appl. No.: 382,447

[22] Filed: Jul. 20, 1989

[30] Foreign Application Priority Data

Jul. 21, 1988 [JP] Japan ................................. 63-182673
Jul. 26, 1988 [JP] Japan ................................. 63-186087

[51] Int. Cl.$^5$ ............................................... G03C 1/08
[52] U.S. Cl. ..................... 430/559; 430/214; 430/216; 430/223; 430/551
[58] Field of Search ............... 430/214, 216, 223, 551, 430/559

[56] References Cited

U.S. PATENT DOCUMENTS 2,701,187  2/1955  Andress .
2,728,659  12/1955  Loria et al. .
3,260,597  7/1966  Weyerts et al. .
4,009,029  2/1977  Hammond et al. .

Primary Examiner—Charles L. Bowers, Jr.
Assistant Examiner—Thomas R. Neville
Attorney, Agent, or Firm—Sughrue, Mion, Zinn, Macpeak & Seas

[57] ABSTRACT

A color light sensitive material which provides a positive dye image having high density, good color reproducibility and which exhibits excellent preservability before use. The material comprises a support having provided thereon a light-sensitive silver halide, a binder, a reducible dye donating compound, and at least one reducing agent selected from the group consisting of a compound represented by formula (IA) and a compound represented by formula (IB):

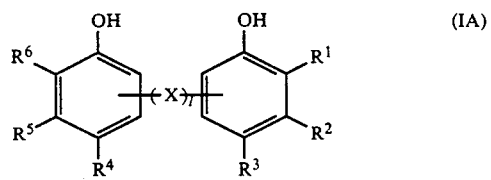

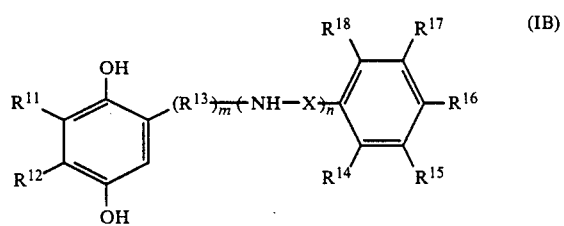

wherein the substituents have the meanings indicated in the specification.

9 Claims, No Drawings

COLOR LIGHT-SENSITIVE MATERIAL

FIELD OF THE INVENTION

This invention relates to a color light-sensitive material and, more particularly, to a color light-sensitive material which provides a positive dye image having high density and good color reproducibility and exhibits excellent preservability before use.

BACKGROUND OF THE INVENTION

There have been proposed many methods for obtaining a positive dye image through a diffusion transfer process. For example, it has been proposed to form a positive dye image by using a system combining a reducible dye donating compound which is capable of releasing a dye with a reducing agent or a precursor thereof, in which wet development or heat development is effected to oxidize the reducing agent in proportion to the exposure amount of silver halide while reducing the dye donating compound with the portion of the reducing agent which remains non-oxidized to thereby release a diffusing dye, as disclosed in U.S. Pat. Nos. 4,559,290, 4,356,249, and 4,358,525, JP-A-53-35533, JP-A-53-110827, JP-A-54-130927, JP-A-56-164342, JP-A-59-154445 and JP-A-62-215270 (the term "JP-A" as used herein means an "unexamined published Japanese patent application"). Further, European Patent Publication No. 220,746 and Kokai-Giho 87-6199 [Vol. 12, No. 22) disclose a heat-developable color light sensitive material using a nondiffusing compound which releases a diffusing dye through a similar mechanism, the nondiffusing compound being capable of releasing a diffusing dye through reductive cleavage of an N-X bond (X represents an oxygen, nitrogen or sulfur atom).

However, when the above-described reducible dye donating compounds are used in combination with a silver halide emulsion together with a reducing agent or a precursor thereof, it has turned out that the developed dye image suffers from considerable stain formation and also such light-sensitive materials have poor preservability before use.

In order to suppress stain formation of the light-sensitive materials for positive image formation using the reducible dye donating compounds, it is effective to use a diffusing electron transport agent in addition to a nondiffusing electron donor as a reducing agent. On the other hand, a radical resulting from the electron transport agent diffuses into other layers having different color sensitivity to cross-oxidize the electron donor present in that layer, thereby causing reduction of image density and deteriorating color reproducibility. Hence, it has been attempted to provide an intermediate layer between light sensitive layers differing in color sensitivity or incorporate a reducing substance in such an intermediate layer. The light-sensitive materials which can be used in a diffusion transfer process, such as those used in the present invention, have limitations with respect to the amounts of binders and reducing substances which can be used in each layer, with image formation rate, resolving power, and film properties being taken into consideration. Further improvements have therefore been demanded.

SUMMARY OF THE INVENTION

One object of this invention is to provide a color light-sensitive material using a reducible dye donating compound, which exhibits improved preservability before use.

Another object of this invention is to provide a color light-sensitive material using a reducible dye donating compound, which provides a positive dye image having increased density and improved color reproducibility.

Other objects and effects of the present invention will be apparent from the following description.

The above objects of this invention can be accomplished by a color light-sensitive material comprising a support having provided thereon a light-sensitive silver halide, a binder, a reducible dye donating compound, and a reducing agent selected from the group consisting of a compound represented by formula (IA) and a compound represented by formula (IB):

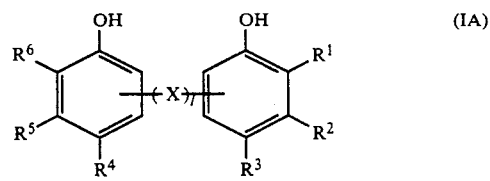

wherein $R^1$, $R^2$, $R^3$, $R^4$, $R^5$, and $R^6$, which may be the same or different, each represents a hydrogen atom, a halogen atom, a hydroxyl group, a substituted or unsubstituted alkyl group, a substituted or unsubstituted aryl group, a substituted or unsubstituted acylamino group, a substituted or unsubstituted alkoxy group, a substituted or unsubstituted aryloxy group, a substituted or unsubstituted alkylthio group, a substituted or unsubstituted arylthio group, a substituted or unsubstituted acyl group, a substituted or unsubstituted sulfonyl group, a substituted or unsubstituted carbamoyl group, or a substituted or unsubstituted sulfamoyl group, provided that at least one of $R^1$ and $R^3$ and at least one of $R^4$ and $R^6$ represent a hydroxyl group; or any adjacent two of $R^1$, $R^2$, $R^3$, $R^4$, $R^5$, and $R^6$ are connected to each other to form a carbocyclic ring; X represents a divalent linking group; and l represents 0 or 1;

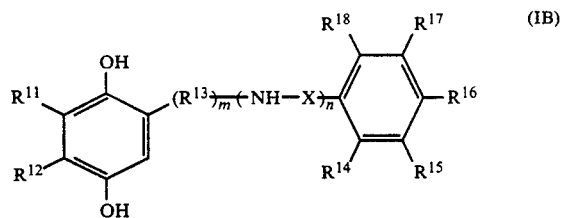

wherein $R^{11}$ and $R^{12}$, which may be the same or different, each represents a hydrogen atom, a halogen atom, a substituted or unsubstituted alkyl group, a substituted or unsubstituted aryl group, a substituted or unsubstituted acylamino group, a substituted or unsubstituted alkoxy group, a substituted or unsubstituted aryloxy group, a substituted or unsubstituted alkylthio group, a substituted or unsubstituted arylthio group, a substituted or unsubstituted acyl group, a substituted or unsubstituted sulfonyl group, a substituted or unsubstituted carbamoyl group, or a Substituted or unsubstituted sulfamoyl group, or $R^{11}$ and $R^{12}$ are taken together to form a carbocyclic ring; $R^{13}$ represents an unsubstituted or alkyl-substituted alkylene group; $R^{14}$, $R^{15}$, $R^{16}$, $R^{17}$, and $R^{18}$, which may be the same or different, each represents a hydrogen atom, a halogen atom, a cyano group, a nitro group, a substituted or unsubstituted alkyl group, a substituted or unsubstituted acylamino group, a substituted or unsubstituted sulfonamido group, a substituted or unsubstituted alkoxy group, a substituted or unsubstituted aryloxy group, a substituted or unsubstituted alkylthio group, a substituted or unsubstituted arylthio group, a substituted or unsubstituted amino group, a substituted or unsubstituted acyl group, a substituted or unsubstituted acyloxy group, a substituted or unsubstituted carbamoyl group, a substituted or unsubstituted carbamoylamino group, a substituted or unsubstituted sulfamoyl group, a substituted or unsubstituted sulfamoylamino group, a substituted or unsubstituted alkoxycarbonyl group, a substituted or unsubstituted aryloxycarbonyl group, a substituted or unsubstituted heterocyclic group, a substituted or unsubstituted alkoxysulfonyl group, or a substituted or unsubstituted aryloxysulfonyl group; $R^{14}$, $R^{15}$, and $R^{16}$ each may further represent a hydroxyl group; or any adjacent two of $R^{14}$, $R^{15}$, $R^{16}$, $R^{17}$, and $R^{18}$ are connected to each other to form a carbocyclic or heterocyclic ring; X represents —CO— or —SO$_2$—; m and n each represents 0 or 1; and the total number of carbon atoms in $R^{11}$, $R^{12}$, $R^{13}$, $R^{14}$, $R^{15}$, $R^{16}$, $R^{17}$, and $R^{18}$ is 8 or more.

DETAILED DESCRIPTION OF THE INVENTION

In formula (IA), at least one of $R^1$ and $R^3$ is a hydroxyl group, and at least one of $R^4$ and $R^6$ is a hydroxyl group. It is preferable that $R^1$ and $R^6$ each represents a hydroxyl group, while $R^3$ and $R^4$ each represents an atom or a group other than a hydroxyl group.

$R^1$, $R^2$, $R^3$, $R^4$, $R^5$, and $R^6$ each preferably represents a hydrogen atom, a halogen atom (e.g., chlorine, bromine, fluorine), a substituted or unsubstituted alkyl group having from 1 to 60 carbon atoms (e.g., methyl, ethyl, propyl, isobutyl, t-butyl, t-octyl, 1-ethylhexyl, nonyl, cyclohexyl, undecyl, pentadecyl, n-hexadecyl, 3-decanamidopropyl, 1-phenylethyl, 2-phenyl-isopropyl), a substituted or unsubstituted aryl group having from 6 to 60 carbon atoms (e.g., phenyl, p-tolyl, naphthyl), a substituted or unsubstituted acylamino group having from 2 to 60 carbon atoms (e.g., acetylamino, n-butanamido, octanoylamino, 2-hexyldecanamido, 2 (2',4'-di-t-amylphenoxy)butanamido, benzoylamino, nicotinamido), a substituted or unsubstituted alkoxyl group having from 1 to 60 carbon atoms (e.g., methoxy, ethoxy butoxy, n-octyloxy, hexadecyloxy, methoxyethoxy), a substituted or unsubstituted aryloxy group having from 6 to 60 carbon atoms (e.g., phenoxy, 2,4-t-amylphenoxy, 4-t-octylphenoxy, naphthoxy), a substituted or unsubstituted alkylthio group having from 1 to 60 carbon atoms (e.g., methylthio, ethylthio, butylthio, hexadecylthio), a substituted or unsubstituted arylthio group having from 6 to 60 carbon atoms (e.g, phenylthio, 4-dodecyloxyphenylthio), a substituted or unsubstituted acyl group having from 2 to 60 carbon atoms (e.g., acetyl, benzoyl, butanoyl, dodecanoyl), a substituted or unsubstituted sulfonyl group having from 1 to 60 carbon atoms (e.g., methanesulfonyl, butanesulfonyl, tolylsulfonyl), a substituted or unsubstituted carbamoyl group having from 1 to 60 carbon atoms (e.g., N,N-dicyclohexylcarbamoyl), a substituted or unsubstituted sulfamoyl group having up to 60 carbon atoms (e.g., N,N-dimethylsulfamoyl), or a hydrogen atom as stated above.

$R^1$ and $R^2$, or $R^2$ and $R^3$, or $R^4$ and $R^5$, or $R^5$ and $R^6$ may be connected to each other to form a carbocyclic ring.

X in formula (IA) represents a divalent linking group, and preferably includes a group of formula $-(Y)_{\overline{m}}$-$Z$-$(Y)_{\overline{m}l}$. In formula (IA), l represents 0 or 1.

In the formula $-(Y)_{\overline{m}}Z-(Y)_{\overline{m}l}$ for the preferred X of formula (IA), Y represents a divalent group selected from

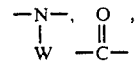

—O—, —SO$_2$—, and a combination of two or more thereof; W represents a substituted or unsubstituted alkyl or aryl group; Z represents a substituted or unsubstituted alkylene or arylene group; and ml represents 0 or 1.

Substituents on Z or W include a nitro group, a halo9en atom (the same as those recited as for $R^1$ to $R^6$), a substituted or unsubstituted alkyl, aryl, acylamino, alkoxy, aryloxy, alkylthio, arylthio, acyl, sulfonyl, carbamoyl or sulfamoyl group (the same as those recited as for $R^1$ to $R^6$), a substituted or unsubstituted amino group having up to 60 carbon atoms (e.g., —NH$_2$, N,N-diethylamino, N,N-dioctadecylamino), a substituted or unsubstituted sulfonamido group having from 2 to 60 carbon atoms (e.g., hexadecanesulfonamido, dodecyloxybenzenesulfonamido), a substituted or unsubstituted acyloxy group having from 2 to 60 carbon atoms (e.g., acetyloxy, benzoyloxy, lauroyloxy), a substituted or unsubstituted alkoxycarbonyl group having from 2 to 60 carbon atoms (e.g., methoxycarbonyl, butoxycarbonyl), a substituted or unsubstituted aryloxycarbonyl group having from 6 to 60 carbon atoms (e.g., phenoxycarbonyl), a substituted or unsubstituted alkoxycarbonyloxy group having from 1 to 60 carbon atoms (e.g., methoxycarbonyloxy); a substituted or unsubstituted aryloxycarbonyloxy group having from 7 to 60 carbon atoms (e.g., phenoxycarbonyloxy), a substituted or unsubstituted alkoxysulfonyl group having from 1 to 60 carbon atoms (e.g., methoxysulfonyl, ethoxysulfonyl), a substituted or unsubstituted aryloxysulfonyl group having from 6 to 60 carbon atoms (e.g., phenoxysulfonyl), a substituted or unsubstituted 5- to 6-membered heterocyclic ring having from 1 to 60 carbon atoms, which may be condensed with other rings, (e.g., furyl, pyridyl, octadecylsuccinimide), a substituted or unsubstituted carbamoylamino group having from 1 to 60 carbon atoms (e.g., N'-dodecylcarbamoylamino), and a substituted or unsubstituted sulfamoylamino group having up to 60 carbon atoms (e.g., N,N'-dipropylsulfamoylamino).

The total number of the carbon atoms in $R^1$, $R^2$, $R^3$, $R^4$, $R^5$, $R^6$, and X is preferably 10 or more, more preferably 14 or more, and is preferably about 30 or less.

Of the compounds represented by formula (IA), preferred are those represented by the following formulae (II), (III), (IV), (V), (VI) and (VII):

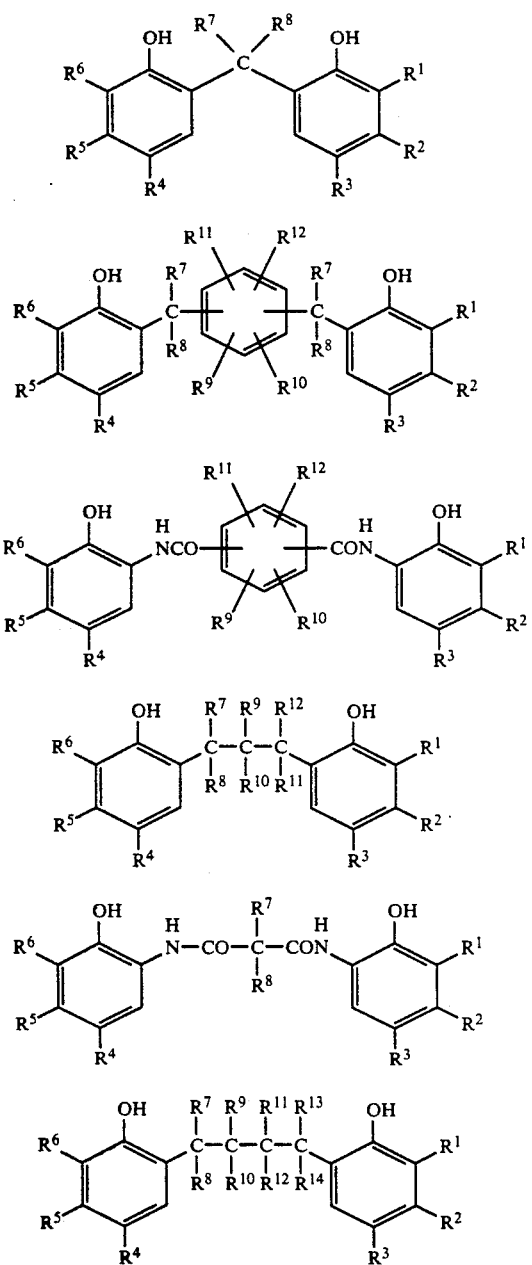

wherein $R^1$, $R^2$, $R^3$, $R^4$, $R^5$, and $R^6$ are as defined above; and $R^7$, $R^8$, $R^9$, $R^{10}$, $R^{11}$, $R^{12}$, $R^{13}$, and $R^{14}$, which may be the same or different, each represents a hydrogen atom, a nitro group, a halogen atom (the same as those recited as for $R^1$ to $R^6$), a substituted or unsubstituted alkyl, aryl, acylamino, alkoxyl, aryloxy, alkylthio, arylthio, acyl, sulfonyl, carbamoyl or sulfamoyl group (the same as those recited as for $R^1$ to $R^6$), or a substituted or unsubstituted amino, sulfonamido, acyloxy, alkoxycarbonyl, aryloxycarbonyl, alkoxycarbonyloxy, aryloxycarbonyloxy, alkoxysulfonyl, aryloxysulfonyl, heterocyclic, carbamoylamino or sulfamoylamino group (the same as those recited as for the substituents on Z or W); or $R^7$ and $R^8$ are connected to each other to form a 5- to 20-membered carbocyclic ring.

More preferred among the compounds of formulae (II) to (VII) are those of formulae (II), (III), and (IV).

$R^5$ or $R^6$ in formulae (II) and (III) each preferably represents a substituted or unsubstituted alkyl or aryl group or a hydrogen atom. $R^7$, $R^8$, $R^9$, or $R^{10}$ in formulae (III) and (IV) each preferably represents a substituted or unsubstituted alkyl, acylamino, sulfonamido, carbamoyl, sulfamoyl or alkoxyl group, a nitro group, a halogen atom, or a hydrogen atom.

Particularly preferred among the compounds of formulae (II), (III), and (IV) are those represented by formula (II).

In formula (II), $R^1$, $R^2$, $R^3$, $R^4$, $R^5$ and $R^6$ each preferably represents a hydrogen atom, a halogen atom, or a substituted or unsubstituted alkyl, alkoxyl or alkylthio group, more preferably a hydrogen atom, a halogen atom, or a substituted or unsubstituted alkyl group. Most preferably, either one of $R^1$ and $R^2$ and either one of $R^3$ and $R^4$ each represents a substituted or unsubstituted alkyl group, with the other representing a hydrogen atom.

In formula (II), $R^7$ and $R^8$ each preferably represents a hydrogen atom or a substituted or unsubstituted alkyl group having from 1 to 30 carbon atoms. When $R^7$ and $R^8$ form a carbocyclic ring, the carbocyclic ring formed by $R^7$ and $R^8$ is preferably a 5 to 12-membered ring. It is more preferred that at least one of $R^7$ and $R^8$ is a substituted or unsubstituted alkyl group. It is the most preferred that at least one of them is a hydrogen atom, with the other being a substituted or unsubstituted alkyl group.

In formula (II), the total carbon atom number of $R^1$ to $R^8$ is preferably 10 or more, more preferably 14 or more, and preferably about 30 or less.

In formula (IB), $R^{11}$ and $R^{12}$ each preferably represents a hydrogen atom, a halogen atom (e.g., chlorine, bromine, fluorine), a substituted or unsubstituted alkyl group having from 1 to 60 carbon atoms (e.g., methyl, t-butyl, t-octyl, cyclohexyl, n-hexadecyl, 3-decanamidopropyl, 1,1-dimethylbenzyl, phenethyl), a substituted or unsubstituted aryl group having from 6 to 60 carbon atoms (e.g., phenyl, p-tolyl), a substituted or unsubstituted acylamino group having from 2 to 60 carbon atoms (e.g., acetylamino, n-butanamido, 2-hexyldecanamido, 2 (2',4'di-t-amylphenoxy)butanamido, benzoylamino), a substituted or unsubstituted alkoxy group having from 1 to 60 carbon atoms (e.g., methoxy, ethoxy, butoxy, t-octyloxy, methoxyethoxy), substituted or unsubstituted aryloxy group having from 6 to 60 carbon atoms (e.g., phenoxy, 4-t-octylphenoxy), substituted or unsubstituted alkylthio group having from 1 to 60 carbon atoms (e.g., butylthio, hexadecylthio), a substituted or unsubstituted arylthio group having from 6 to 60 carbon atoms (e.g., phenylthio, 4-dodecyloxyphenylthio), a substituted or unsubstituted acyl group having from 2 to 60 carbon atoms (e.g., acetyl, benzoyl, lauroyl), a substituted or unsubstituted sulfonyl group having from 1 to 60 carbon atoms (e.g., methanesulfonyl, octanesulfonyl, benzenesulfonyl, dodecylbenzenesulfonyl), a substituted or unsubstituted carbamoyl group having from 1 to 60 carbon atoms (e.g., N,N-dicyclohexylcarbamoyl) or a substituted or unsubstituted sulfamoyl group having up to 60 carbon atoms (e.g., t-butylsulfamoyl). $R^{11}$ and $R^{12}$ in formula (IB) may be connected to each other to form a carbocyclic ring.

$R^{13}$ in formula (IB) preferably represents an alkyl-substituted or unsubstituted alkylene group having from 1 to 5 carbon atoms (e.g., methylene, ethylene, 1-methylethylene).

$R^{14}$, $R^{15}$, $R^{16}$, $R^{17}$, and $R^{18}$ in formula (IB) each preferably represents a hydrogen atom, a halogen atom (e.g., chlorine, bromine, fluorine), a cyano group, a nitro group, a substituted or unsubstituted alkyl group having from 1 to 60 carbon atoms (e.g., cyclohexyl, dodecyl, octadecyl, 3-(N,N-dihexylcarbamoyl)propyl), a substituted or unsubstituted acylamino group having from 2 to 60 carbon atoms (e.g., octanoylamino, 2-hexyldecanoylamino, benzoylamino, nicotinamido), a substituted or unsubstituted sulfonamido group having from 1 to 60 carbon atoms (e.g., hexadecanesulfonamido, dodecyloxybenzenesulfonamido), a substituted or unsubstituted alkoxy group having from 1 to 60 carbon atoms (e.g., methoxy, n-butoxy, hexadecyloxy, 2-methoxyethoxy), a substituted or unsubstituted aryloxy group having from 6 to 60 carbon atoms (e.g., phenoxy, 4 t-octylphenoxy), a substituted or unsubstituted alkylthio group having from 1 to 60 carbon atoms (e.g., methylthio), a substituted or unsubstituted arylthio group having from 6 to 60 carbon atoms (e.g., phenylthio), a substituted or unsubstituted amino group having up to 60 carbon atoms (e.g., $-NH_2$, N,N-diethylamino, N,N-dioctadecylamino), a substituted or unsubstituted acyl group having from 2 to 60 carbon atoms (e.g., acetyl, benzoyl, lauroyl), a substituted or unsubstituted acyloxy group having from 2 to 60 carbon atoms (e.g., acetyloxy, benzoyloxy, lauroyloxy), a substituted or unsubstituted carbamoyl group having from 1 to 60 carbon atoms (e.g., N,N-dicyclohexylcarbamoyl, N,N-dioctylcarbamoyl), a substituted or unsubstituted carbamoylamino group having from 1 to 60 carbon atoms (e.g., N'-dodecylcarbamoylamino), a substituted or unsubstituted sulfamoyl group having up to 60 carbon atoms (e.g., N,N-dibutylsulfamoyl), a substituted or unsubstituted sulfamoylamino group having up to 60 carbon atoms (e.g., N',N'-dipropylsulfamoylamino), a substituted or unsubstituted alkoxycarbonyl group having from 2 to 60 carbon atoms (e.g., methoxycarbonyl, butoxycarbonyl), a substituted or unsubstituted aryloxycarbonyl group having from 7 to 60 carbon atoms (e.g., phenoxycarbonyl), a substituted or unsubstituted 5- to 6-membered heterocyclic group having from 1 to 60 carbon atoms which may have a condensed ring (e.g., octadecylsuccinimide, furyl, pyridyl), a substituted or unsubstituted aryloxycarbonyloxy group having from 7 to 60 carbon atoms (e.g., phenoxycarbonyloxy), a substituted or unsubstituted alkoxysulfonyl group having from 1 to 60 carbon atoms (e.g., methoxysulfonyl, ethoxysulfonyl), or a substituted or unsubstituted aryloxysulfonyl group having from 6 to 60 carbon atoms (e.g., phenoxysulfonyl). In addition, $R^{14}$, $R^{15}$, or $R^{16}$ in formula (IB) further represents a hydroxyl group. Any adjacent two of $R^{14}$, $R^{15}$, $R^{16}$, $R^{17}$, and $R^{18}$ in may be taken together to form a carbocyclic or heterocyclic ring.

X in formula (IB) represents $-CO-$ or $-SO_2-$.

m and n in formula (IB) each represents 0 or 1.

The total number of the carbon atoms in $R^{11}$ $R^{12}$, $R^{13}$, $R^{14}$, $R^{15}$, $R^{16}$, $R^{17}$, and $R^{18}$ in formula (IB) is at least 8, and preferably about 30 or less.

The compounds of formula (IB) embrace dimers, trimers or polymers comprising a unit represented by formula (IB).

$R^{11}$ and $R^{12}$ in formula (IB) each preferably represents a hydrogen atom, a halogen atom, or a substituted or unsubstituted alkyl, alkoxyl or alkylthio group, more preferably a hydrogen atom, a halogen atom, or a substituted or unsubstituted alkyl group, most preferably a substituted or unsubstituted alkyl group.

$R^{13}$ in formula (IB) preferably contains not more than 3 carbon atoms.

$R^{14}$, $R^{15}$, $R^{16}$, $R^{17}$, and $R^{18}$ in formula (IB) each preferably represents a hydrogen atom or a substituted or unsubstituted alkyl, acylamino, sulfonamido, alkoxyl, acyloxy, carbamoyl, sulfamoyl, alkoxycarbonyl or alkoxysulfonyl group, more preferably a hydrogen atom or a substituted or unsubstituted alkyl, acylamino, sulfonamido, carbamoyl or alkoxycarbonyl group. It is very preferred that $R^{14}$ and $R^{16}$ in formula (IB) represents a hydroxyl group.

m in formula (IB) very preferably represents 1, and relatively preferably represents 0.

The total number of the carbon atoms in $R^{11}$, $R^{12}$, $R^{13}$, $R^{14}$, $R^{15}$, $R^{16}$, $R^{17}$, and $R^{18}$ in formula (IB) is preferably 12 or more, more preferably 16 or more, and preferably about 30 or less.

Specific examples of compounds represented by formula (IA) are shown below for illustrative purposes only but not for limitation.

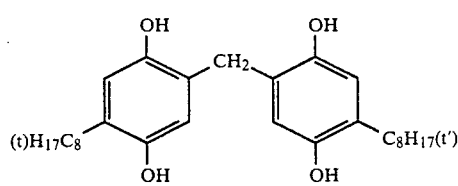

A-(1)

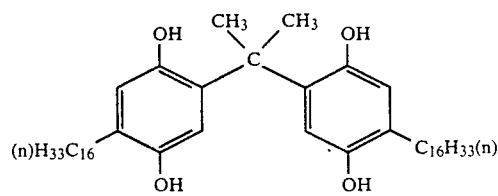

A-(2)

-continued
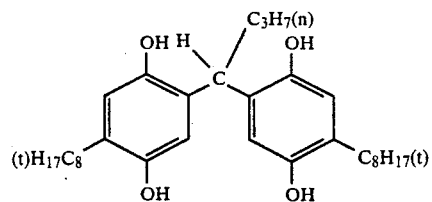 A-(3)
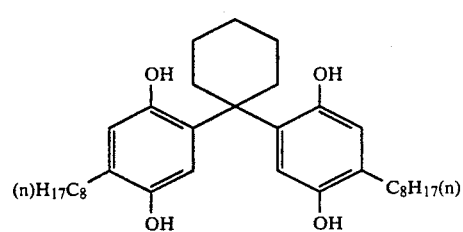 A-(4)
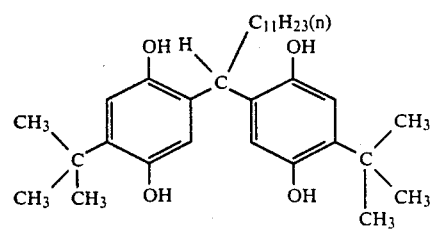 A-(5)
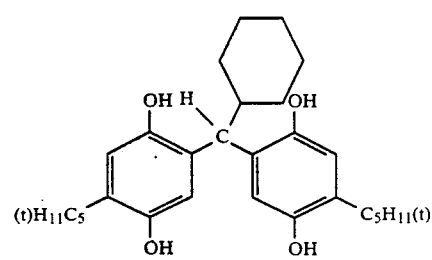 A-(6)
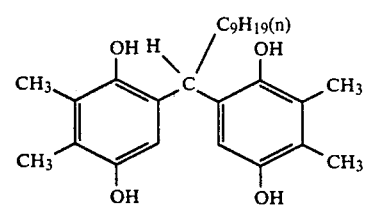 A-(7)
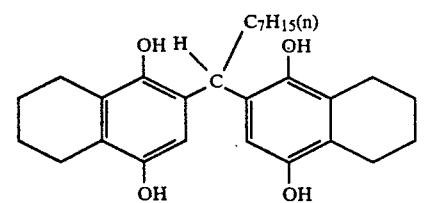 A-(8)
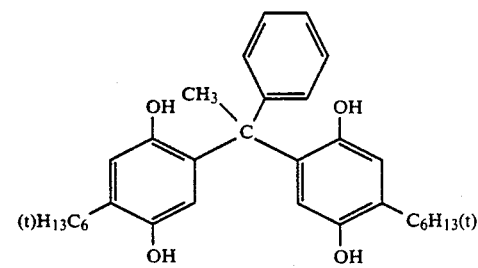 A-(9)

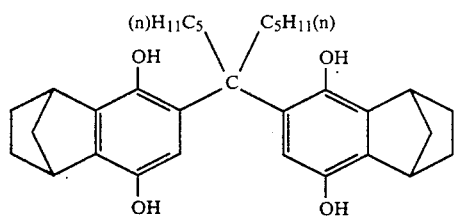
A-(10)
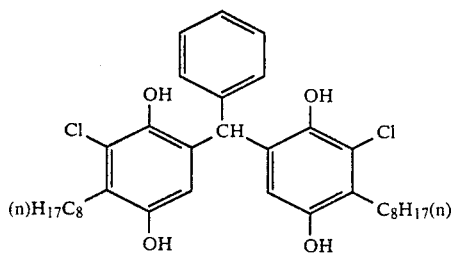
A-(11)
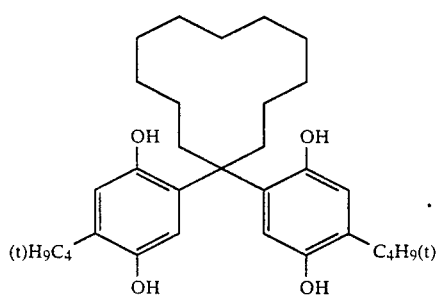
A-(12)
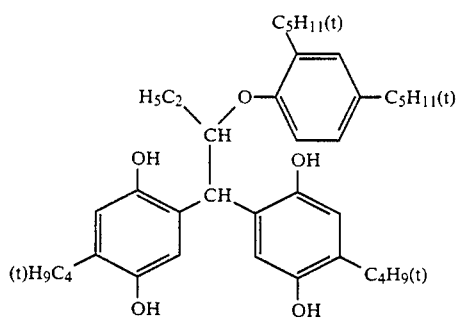
A-(13)
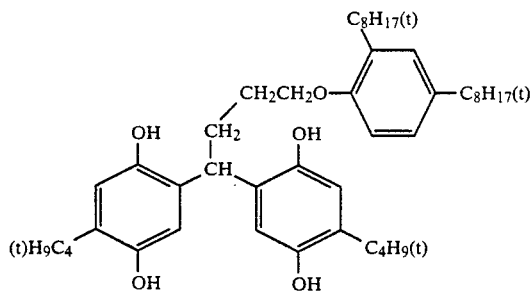
A-(14)
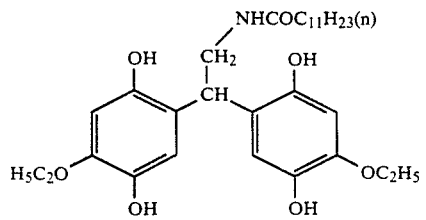
A-(15)

-continued
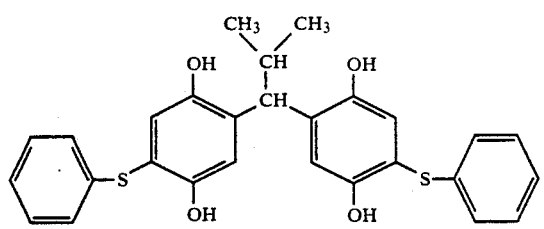
A-(16)
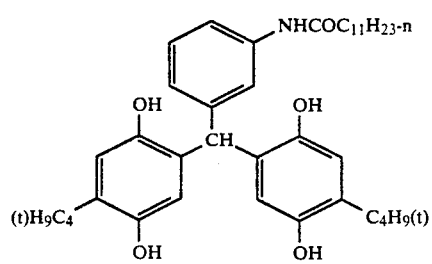
A-(17)
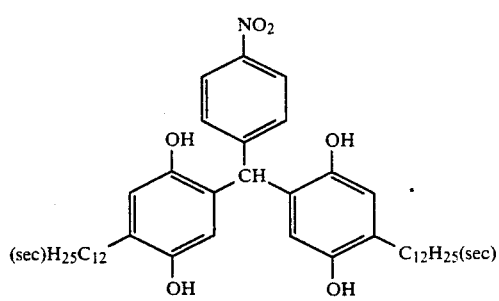
A-(18)
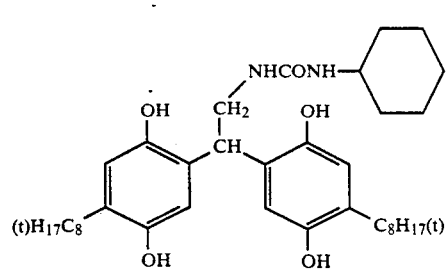
A-(19)
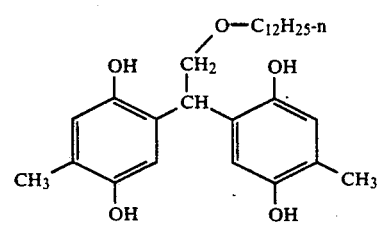
A-(20)
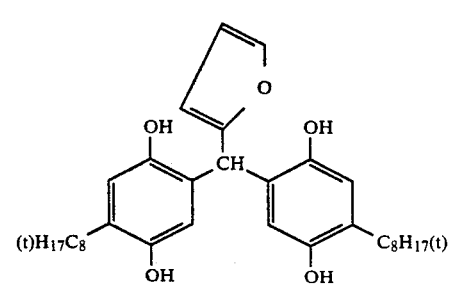
A-(21)

-continued
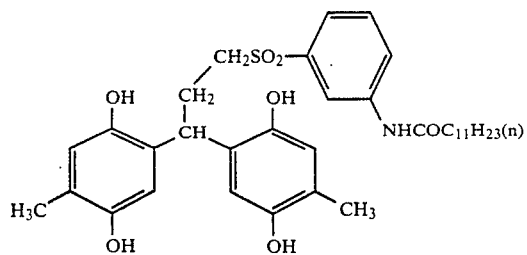
A-(22)
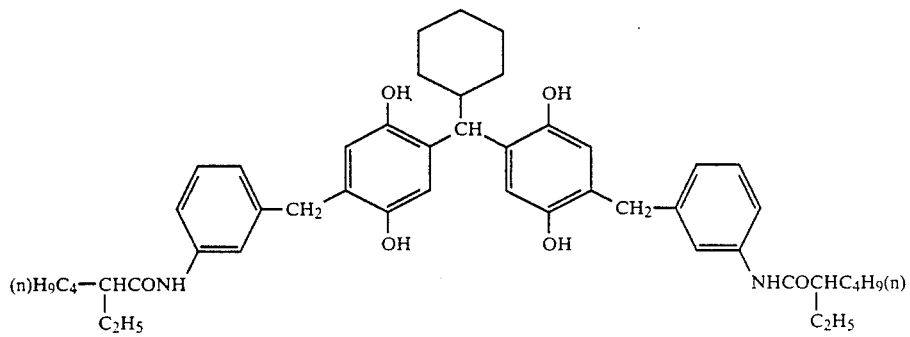
A-(23)
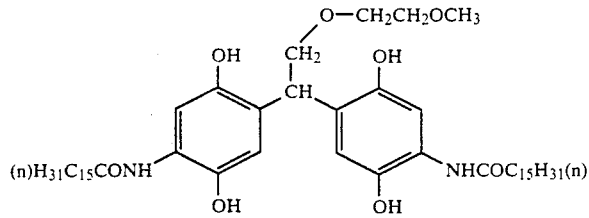
A-(24)
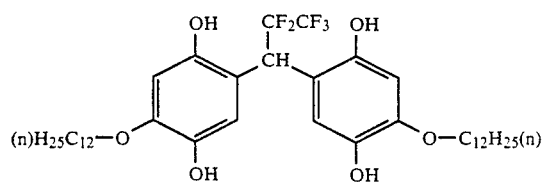
A-(25)
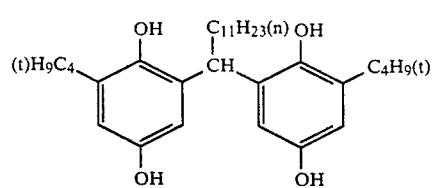
A-(26)
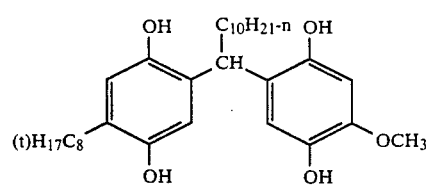
A-(27)
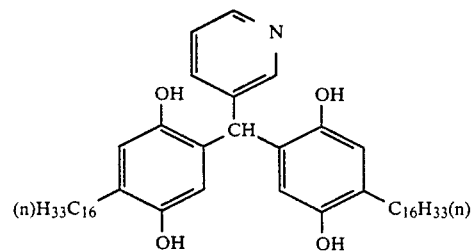
A-(28)

-continued
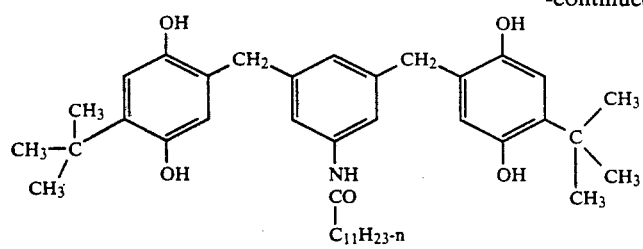 A-(29)
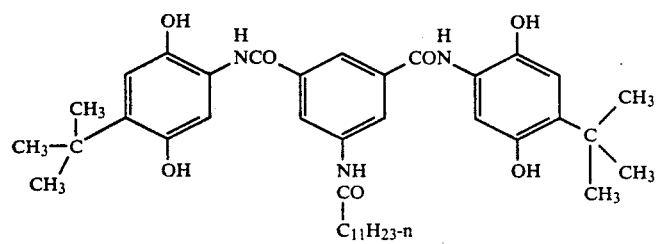 A-(30)
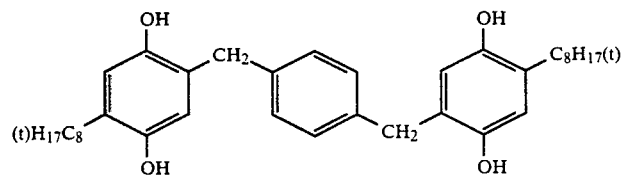 A-(31)
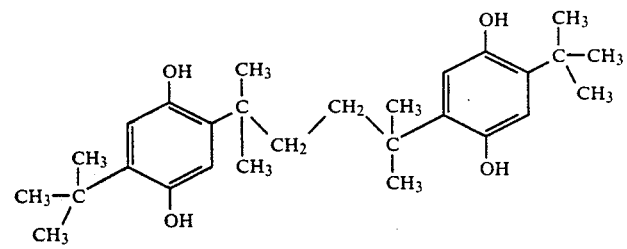 A-(32)
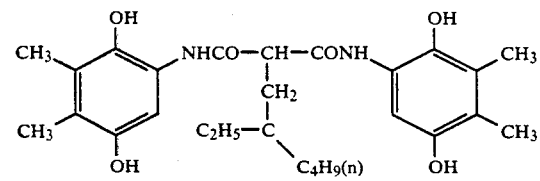 A-(33)
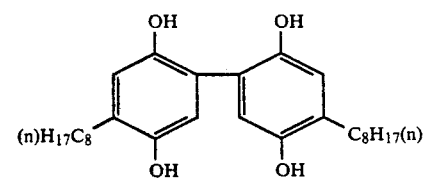 A-(34)
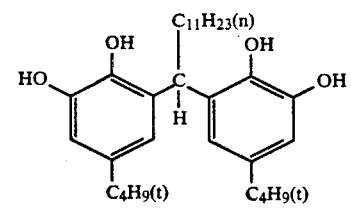 A-(35)
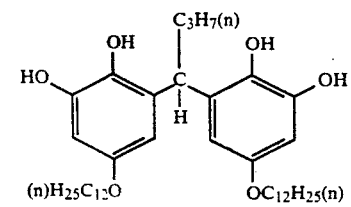 A-(36)

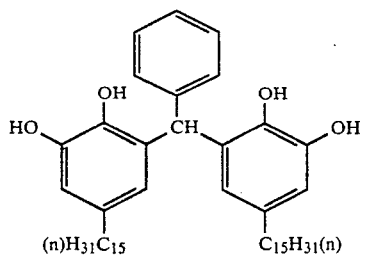
A-(37)
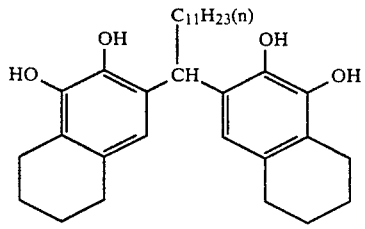
A-(38)
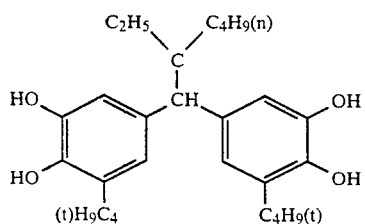
A-(39)
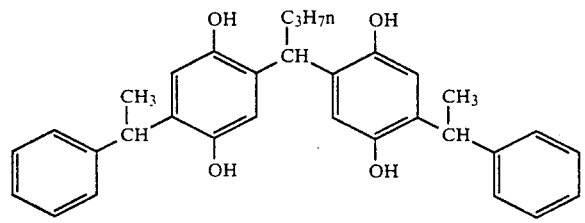
A-(40)
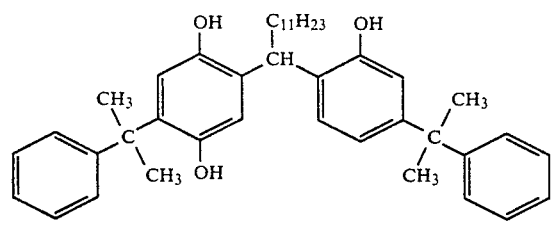
A-(41)
Specific examples of compounds represented by formula (IB) are shown below for illustrative purposes only but not for limitation.
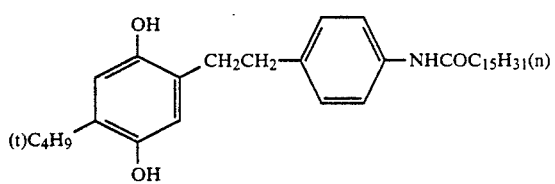
B-(1)
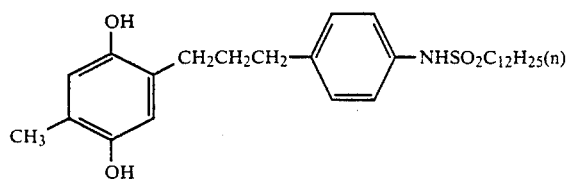
B-(2)

-continued
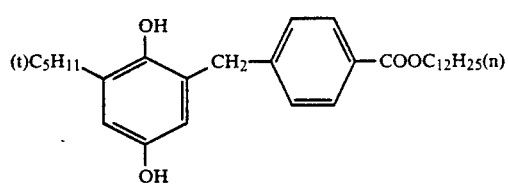
B-(3)
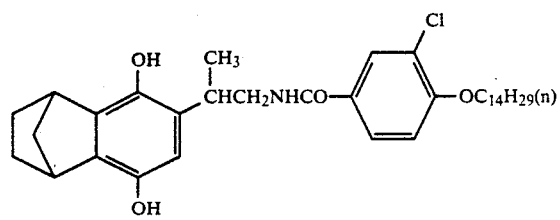
B-(4)
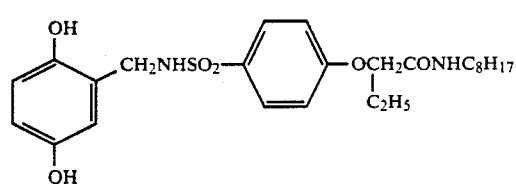
B-(5)
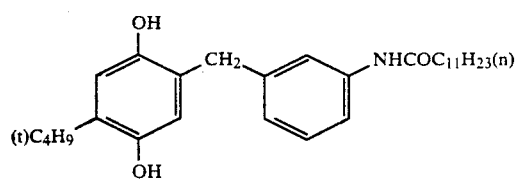
B-(6)
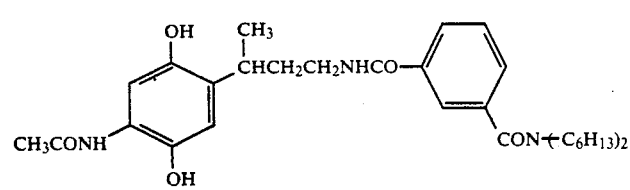
B-(7)
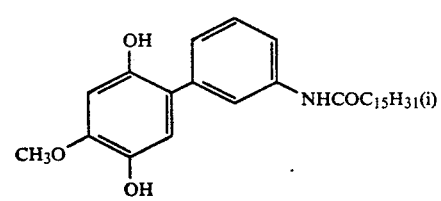
B-(8)
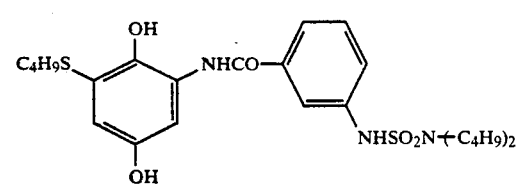
B-(9)
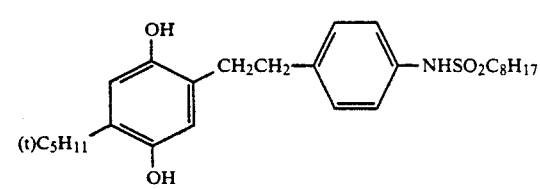
B-(10)

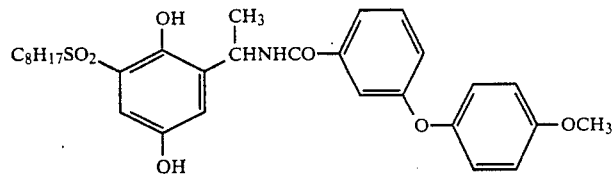 B-(11)
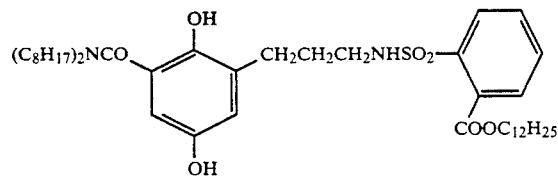 B-(12)
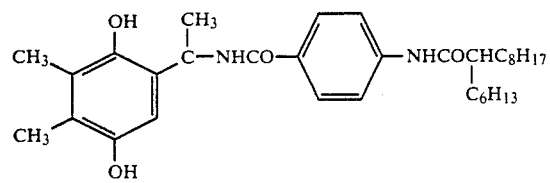 B-(13)
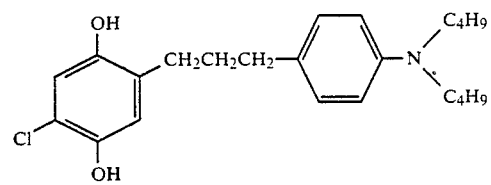 B-(14)
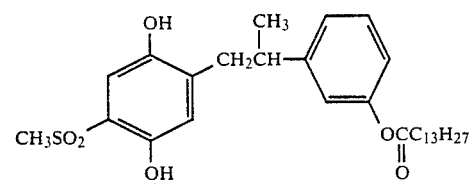 B-(15)
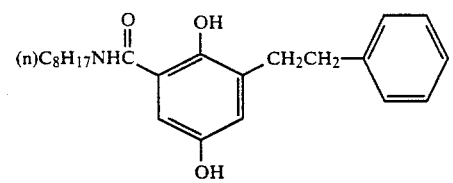 B-(16)
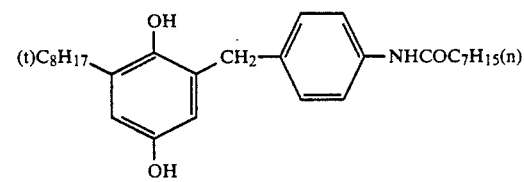 B-(17)
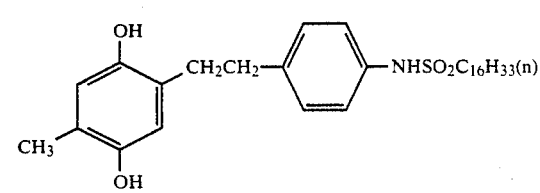 B-(18)

-continued
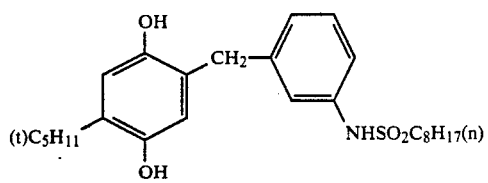
B-(19)
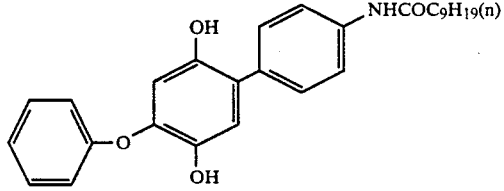
B-(20)
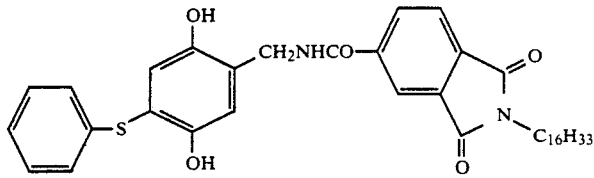
B-(21)
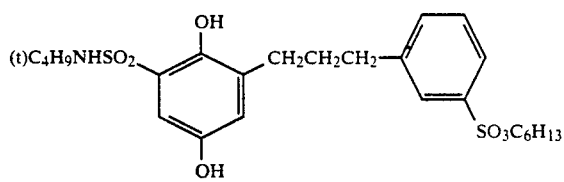
B-(22)
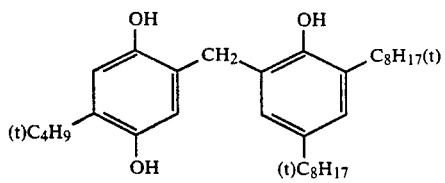
B-(23)
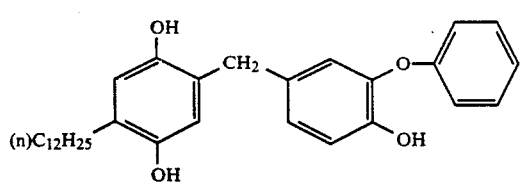
B-(24)
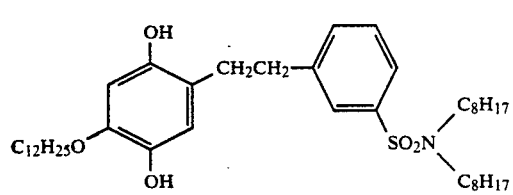
B-(25)
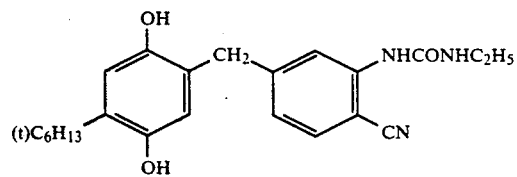
B-(26)

-continued

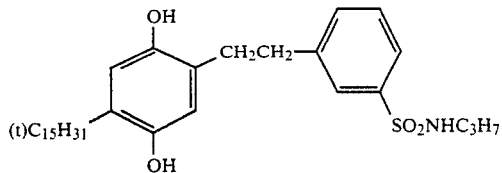
B-(27)

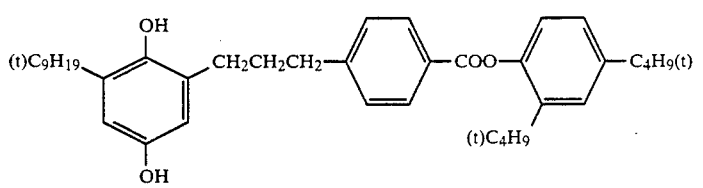
B-(28)

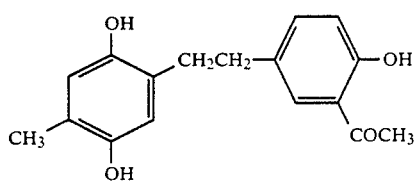
B-(29)

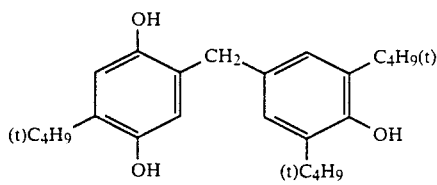
B-(30)

Typical examples of synthesis of the compounds of formulae (IA) and (IB) are described below but the synthesis of the compounds is not construed as being limited to these Synthesis Examples. Other compounds of formulae (IA) and (IB) than those described below can be synthesized by the similar process as described below.

SYNTHESIS EXAMPLE 1

Synthesis of Compound A-(5)

In 40 ml of ethyl acetate were dissolved 16.6 g of t-butylhydroquinone and 13.8 g of 1-dodecanal, and 4 ml of concentrated hydrochloric acid was added to the solution, followed by stirring at room temperature for 8 hours. The reaction mixture was poured into water and extracted with ethyl acetate. The organic layer was dried over anhydrous sodium sulfate and concentrated. Recrystallization of the residue from n-hexane/ethyl acetate (10/1 by volume) yielded 15.7 g .of Compound A-(5) as a white crystal having a melting point of 163° C.

SYNTHESIS EXAMPLE 2

SYnthesis of Compound A-(3)

In 100 ml of ethyl acetate were dissolved 40 g of t-butylhydroquinone and 13 g of 1-butanol, and 7.2 ml of concentrated hydrochloric acid were added thereto, followed by stirring at room temperature for 7 hours. The reaction mixture was worked up in the same manner as in Synthesis Example 1, and the crude product was recrystallized from n-hexane/ethyl acetate (6/1 by volume) to obtain 21 g of Compound A-(3) as a white crystal (which blackens at 200° C. or higher).

SYNTHESIS EXAMPLE 3

Synthesis of Compound A-(7)

In 150 ml of ethyl acetate were dissolved 27.6 g of 2,3-dimethylhydroquinone and 20 g of 1-dodecanal at 30° C., and 10 ml of concentrated hydrochloric acid were added thereto, followed by stirring at room temperature for 5 hours. After completion of the reaction, the reaction mixture was worked up in the same manner as in Synthesis Example 1, and the crude product was recrystallized from n-hexane/ethyl acetate (10/1 by volume) to obtain 13 g of Compound A-(7) as a white crystal having a melting point of 171° C.

SYNTHESIS EXAMPLE 4

Synthesis of Compound B-(6)

(a) Synthesis of 2,5-Dimethoxy-3'-nitrobenzophenone:

In a 3 l-volume three-necked flask were charged 372 g of m-nitrobenzoyl chloride and 280 g of p-dimethoxybenzene, and 1.6 l of methylene chloride were added thereto to form a solution. To the solution were added dropwise 300 g of aluminum chloride over about 1 hour while stirring at room temperature. The reaction mixture slightly generated heat, and the methylene chloride began to reflux. After stirring was continued for about 2 hours, the reaction mixture was allowed to stand overnight.

The reaction mixture was poured on 1 kg of ice, followed by liquid-liquid separation. The separated methylene chloride layer was distilled on a steam bath to remove the solvent. The residue was poured into 1 l of water while hot to precipitate crystals, which were collected by filtration, washed with water, and recrystallized from 1.5 l of ethanol to obtain 470 g of the entitled compound as a pale yellow crystal having a melting point of 98° C.

(b) Synthesis of 2,5-Dimethoxy-3'-aminobenzhydrol:

In a 2 l-volume autoclave equipped with a stirrer were charged 100 g of 2,5-dimethoxy-3'-nitrobenzophenone as obtained in (a) above, 2 g of 10% palladium-on-carbon, and 1.3 l of ethanol. After the atmosphere was displaced twice with hydrogen, hydrogen was introduced thereinto to an inner pressure of 100 kg/cm$^2$. The mixture was heated up to 130° C. while stirring, and the stirring was continued for 8 hours, followed by allowing to cool overnight. The reaction mixture was taken out, and the catalyst was removed by filtration. The filtrate was concentrated to dryness. On addition of 70 ml of ethanol to the residue, a white crystal was precipitated. The crystal was collected by filtration and air-dried to recover 48 g of the entitled compound having a melting point of 132° to 134° C.

(c) Synthesis of 2,5-Dimethoxy-3'-aminodiphenylmethane:

In a 2 l-volume three-necked flask was put 300 ml of acetic acid, and 96 g of a zinc powder were slowly added thereto while vigorously stirring. Then, 49.5 g of 2,5-dimethoxy-3'-aminobenzhydrol as prepared in (b) above were put therein. After the mixture was heated up to 60° C., 240 ml of 35% hydrochloric acid were added dropwise thereto over 15 minutes. After the mixture was stirred for 30 minutes, 240 ml of 35% hydrochloric acid were further added dropwise thereto. The mixture was stirred at 90° C. for 2 hours, followed by cooling. The supernatant liquor was separated and neutralized to a pH of 5 with a sodium hydroxide aqueous solution consisting of 70 g of sodium hydroxide and 600 ml of water. The oily substance thus precipitated was extracted with ethyl acetate, and the extract was washed 6 times with a sodium bicarbonate aqueous solution, dried over sodium sulfate, and filtered. The filtrate was concentrated and distilled under reduced pressure. A fraction having a boiling point of 170° to 175° C./1 mmHg was put in a dish for crystallization to obtain 35 g of the entitled compound having a melting point of 81° to 84° C.

(d) Synthesis of 2,5-Dihydroxy-3'-aminodiphenylmethane:

Twenty seven grams of 2,5-dimethoxy-3'-aminodiphenylmethane as synthesized in (c) above were mixed with 210 ml of 46% hydrobromic acid in a 1 l-volume eggplant type flask to precipitate a salt. The mixture was refluxed at an oil bath temperature of 150° C. for 1 to 2 hours in a nitrogen stream whereby the salt was dissolved to form a pale brown solution. On cooling, a crystal was precipitated, which was collected by filtration. The crystal was placed in a 1 l beaker and dissolved in 200 ml of water. Addition of 25 g of sodium acetate for neutralization resulted in release of an amine compound. The precipitate was collected by filtration, air-dried, and recrystallized from ethanol/benzene (⅓ by volume) to give 16 g of the entitled compound having a melting point of 151° to 152° C.

(e) Synthesis of 2,5-Dihydroxy 3'-laurylamidodiphenylmethane:

In a 300 ml-volume three-necked flask were charged 15 g of the product obtained in (d) above, 6 ml of pyridine, 30 ml of acetonitrile, and 30 ml of dimethylacetamide, and 14.5 g of lauroyl chloride were slowly added dropwise to the mixture while stirring. After 1 hour stirring, a hydrochloric acid aqueous solution comprising 10 ml of 35% hydrochloric acid and 100 ml of water were added to the reaction mixture, and the stirring was further continued, whereby an oily substance was separated and gradually crystallized. When sufficient crystallization was reached, the crystal was collected by filtration, washed with water, and dried to obtain 25 g of the entitled compound having a melting point of 122 to 123° C.

(f) Synthesis of Compound B-(6):

In a 300 ml-volume three-necked flask were charged 25 g of the product as synthesized in (e) above, 24 g of t-butanol, and 130 ml of ethyl acetate, and 27.5 ml of concentrated sulfuric acid were slowly added dropwise thereto while stirring. After the dropwise addition, the reaction mixture was heated to 35° C., and the stirring was continued for 4 hours. The reaction mixture was poured in 200 ml of ice-water in a beaker to effect liquid-liquid separation. The separated ethyl acetate layer was washed three times with water and dried over magnesium sulfate overnight. The ethyl acetate was removed by distillation under reduced pressure, and the residue was recrystallized from 130 ml of a mixed solvent of n-hexane and ethyl acetate (20:1 by volume) to obtain 11.6 g of Compound B-(6) having a melting point of 141° to 142° C.

Elementary Analysis for $C_{29}H_{43}NO_3$:
Calcd. (%): C 76.78; H 9.55; N 3.0;
Found (%): C 76.52; H 9.61; N 3.02.

SYNTHESIS EXAMPLE 5

Synthesis of Compound B-(10)

(a) Synthesis of (4-Octanesulfonamidophenethyl)hydroquinone:

In 1 l-volume three-necked flask were charged 100 g of (4-aminophenethyl)hydroquinone, 500 ml of dimethylacetamide, and 36 ml of pyridine, and 85 ml of octanesulfonyl chloride were slowly added dropwise thereto at room temperature while stirring. After the dropwise addition, the stirring was continued for 4 hours. The reaction mixture was poured into a hydrochloric acid aqueous solution and extracted with ethyl acetate. The extract was washed with water, dried over magnesium sulfate, and concentrated to obtain 129 g of the entitled compound as an oily substance.

(b) Synthesis of Compound B-(10):

In a 1 l-volume three-necked flask were charged 129 g of the product as prepared in (a) above and 400 ml of ethyl acetate, and 50 ml of concentrated sulfuric acid were slowly added dropwise thereto under cooling to 30° C or lower with water. Then, 180 ml of 2-methyl-1-butene were added dropwise to the reaction mixture, and the mixture was stirred at room temperature for 12 hours, and then allowed to stand overnight. The reaction mixture was poured into a hydrochloric acid aqueous solution and extracted with ethyl acetate. The extract was washed with water, dried over magnesium sulfate, and concentrated. The concentrate was purified by silica gel column chromatography using a mixed solvent of chloroform and ethyl acetate (20:1 by volume) as a developing solvent, followed by concentration to obtain 106 g of Compound B-(10) as a pale brown oily substance.

Elementary Analysis for $C_{27}H_{41}NO_4S$:
CalCd. (%): C 68.17; H 8.69; N 2.95;
Found (%): C 68.51; H 8.60; N 2.83.

The reducing agent according to the present invention is used in an amount of from 0.001 to 20 mols, preferably from 0.01 to 10 mols, per mol of silver; or in an amount of from 0.05 to 10 mols, preferably from 0.1 to 5 mols, per mol of the reducible dye donating substance.

The reducing agent of the present invention may be used in combination with known reducing agents. Examples of usable known reducing agents or precursors thereof are described, e.g., in U.S. Pat. Nos. 4,500,626 (col. 49 to 50), 4,483,914 (col. 30 to 31), 4,330,617, and 4,590,152, JP-A-60-140335 (pp. 17 to 18), JP-A-57-40245, JP-A-56-138736, JP-A 59-178458, JP-A-59-53831, JP-A-59-182449, JP-A-59-182450, JP-A-60-119555, JP-A-60-128436, JP-A-60-128437, JP A-60-128438, JP-A-60-128439, JP-A-60-198540, JP-A-60-181742, JP-A-61-259253, JP-A-62-244044,and JP-A-62-13253 to JP-A-62-131256, and European Patent 220,746A2 (pp. 78 to 96).

Since the reducing agent of the present invention is of low diffusibility, it is preferable to use it in combination with an electron transport agent and/or a precursor thereof so as to accelerate electron transfer between the reducing agent (electron donor) of the invention and developable silver halide.

The electron transport agent or a precursor thereof can be selected from among the above-described known reducing agents and precursors thereof. The electron transport agent or a precursor thereof preferably exhibits greater mobility than the nondiffusion reducing agent (electron donor). Particularly useful electron transport agents are 1 phenyl-3-pyrazolidones and aminophenols.

The combination of the electron donor of the present invention and the electron transport agent or a precursor thereof is preferably incorporated into the color light-sensitive material. Each of the electron donor and the electron transport agent or a precursor thereof may be used either individually or in combination of two or more thereof. They can be incorporated into every one of or some of the emulsion layers of the light-sensitive material (e.g., blue-, green-, red-, infrared- and ultraviolet-sensitive layers) or any layer adjacent to emulsion layers (e.g., antihalation layer, subbing layer, intermediate layer, protective layer) or all of these layers. The electron donor and the electron transport agent may be incorporated into the same layer or different layers. Further, the reducing agent may be incorporated into the layer to which the dye donating compound is added or a different layer. It is desirable that the nondiffusion electron donor be present in the layer into which the dye donating compound is incorporated.

The electron transport agent can also be incorporated into an image-receiving material (dye-fixing layer). In cases where a solvent is used at the time of development, the electron transport agent may be present in the solvent in a dissolved state.

The reducible dye donating compound to be used in this invention is a nondiffusion compound capable of releasing a diffusing dye on reaction with the portion of the reducing agent which remains non-oxidized by development as stated in U.S. Pat. No. 4,559,290, EP-A2-220746, and Kokai-Giho 87-6199.

The reducible dye donating compound includes compounds capable of releasing a diffusing dye through intramolecular nucleophilic substitution after the reduction reaction thereof as described in U.S. Pat. Nos. 4,139,389 and 4,139,379 and JP-A-59-185333 and JP-A-57-84453; compounds capable of releasing a diffusing dye through intramolecular electron transfer after the reduction reaction thereof as described in U.S. Pat. No. 4,232,107, JP-A-59-101649 and JP-A-61-88257, and Research Disclosure (hereinafter abbreviated as RD) 24025 (1984); compounds capable of releasing a diffusing dye on cleavage of a single bond after the reduction reaction thereof as described in West German Patent 3,008,588A, JP-A-56-142530, and U.S. Pat. Nos. 4,343,893 and 4,619,884; nitro compounds capable of releasing a diffusing dye on receipt of an electron as described in U.S. Pat. No. 4,450,223; and compounds capable of releasing a diffusing dye on receipt of an electron as described in U.S. Pat. No. 4,609,610.

Preferred reducible dye donating compounds include compounds having an N—X bond (X represents an oxygen, sulfur or nitrogen atom) and an electron attractive group per molecule as disclosed in EP-A2-220,746, Kokai-Giho 87-6199 and JP-A-63-201653, JP-A-63-201654; compounds having an $SO_2$—X bond (X has the same meaning as defined above in the N—X bond) and an electron attractive group per molecule as disclosed in JP-A-1-26842; compounds having a C—X' bond (X' represents oxygen, sulfur, nitrogen, or $SO_2$—) and an electron attractive group per molecule as disclosed in JP-A-63-271344.

Particularly preferred reducible dye donating compounds are the compounds having an N—X bond and an electron attractive group per molecule. Specific examples of such compounds are enumerated in European Patent 220,7465A2 as compound Nos. (1) to (3), (7) to (10), (12), (13), (15), (23) to (26), (31), (32), (35), (36), (40), (41), (44), (53) to (59), (64), and (70), and in Kokai-Giho 87-6199 as compound Nos. (11) to (23).

The hydrophobic additives, such as dye donating compounds and the nondiffusion reducing agents of the present invention, can be introduced into layers of a light-sensitive element according to known methods as described, e.g., in U.S. Pat. No. 2,322,027. In some detail, a high-boiling organic solvent can be used, if desired, in combination with a low-boiling organic solvent having a boiling point of from 50° to 160° C. as described in JP-A-59-83154, JP-A-59-178451, JP-A-59-178452, JP-A-59-178453, JP-A-59-178454, JP-A-59-178455 and JP-A-59-178457. The high-boiling organic solvent to be used preferably has a viscosity of 50 cps or more and a dielectric constant of 10 or less. Specific examples of such a high-boiling organic solvent are listed below.

| | Viscosity (cps) | Dielectric Constant |
|---|---|---|
| $(n\text{-}C_{14}H_{29}O)_3P=O$ | 189 | 4.01 |
| $(C_9H_{19}\text{-}C_6H_4\text{-}O)_3P=O$ | 15600 | 5.08 |

-continued

| | Viscosity (cps) | Dielectric Constant |
|---|---|---|
| 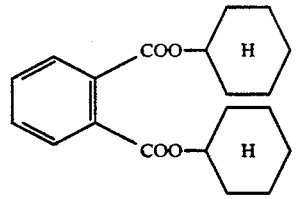 | solid | 6.45 (supercooled liquid) |
| 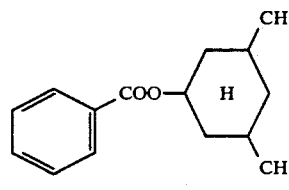 | solid | 5.32 (supercooled liquid) |
| 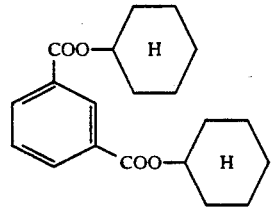 | 10700 | 5.84 |
| CH$_2$COOC$_{13}$H$_{27}$(iso)<br>\|<br>HO—C—COOC$_{13}$H$_{27}$(iso)<br>\|<br>CH$_2$COOC$_{13}$H$_{27}$(iso) | 390 | 4.12 |

The amount of the high boiling organic solvent to be used is not more than 10 g, preferably not more than 5 g, per gram of the dye donating compound; and is preferably not more than 1 cc, more preferably not more than 0.5 cc, most preferably not more than 0.3 cc, per gram of a binder.

Introduction of the hydrophobic compounds can also be carried out by a dispersion method using a polymer as disclosed in JP-B-51-39853 (the term "JP-B" as used herein means an "examined published Japanese Patent application") and JP-A-51-59943.

In cases where the compounds are substantially water-insoluble, they may be introduced as finely dispersed in a binder as well as the above-described methods.

When the hydrophobic compounds are dispersed in a hydrophilic colloid, various types of surface active agents can be employed. For example, the surface active agents recited in JP-A-59-157636 (pp. 37 to 38) can be used.

The light-sensitive material according to the present invention essentially comprises a support having provided thereon a light-sensitive silver halide, a binder, a reducing agent, a reducible dye donating compound, and a high-boiling organic solvent. While these components are usually incorporated into the same layer, they may be divided and added in separate layers as long as they are ready to undergo reactions. For instance, incorporation of a colored dye donating compound into a layer beneath a silver halide emulsion layer is effective to prevent reduction of sensitivity. The reducing agent can be added to not only an emulsion layer but an intermediate layer to thereby improve color reproducibility.

In order to obtain a color of broad range within a chromaticity diagram by use of three primary colors, i.e., yellow, magenta and cyan, at least three silver halide emulsion layers differing in color sensitivity are combined. For example, a blue-sensitive layer, a green-sensitive layer, and a red-sensitive layer are combined, or a green-sensitive layer, a red-sensitive layer, and an infrared-sensitive layer are combined. These light-sensitive layers are built up in various orders known in general color light-sensitive materials. If desired, each of the light-sensitive layers may be divided into two or more layers.

In addition to the light-sensitive layers, the light-sensitive material may have auxiliary layers such as a protective layer, a subbing layer, an intermediate layer, a yellow filter layer, an antihalation layer, and a backing layer.

The silver halide which can be used in the present invention may be any of silver chloride, silver bromide, silver iodobromide, silver chlorobromide, silver chloroiodide, and silver chloroiodobromide.

The silver halide emulsion which can be used in the present invention may be either a surface latent image type emulsion or an internal latent image type emulsion. The internal latent image type emulsion is used as a direct reversal emulsion in combination with a nucleating agent and light fog. The internal latent image type emulsion may be a so called core-shell type emulsion in which the interior and the outer shell of grains are different in halogen composition. The silver halide emulsion may be either a monodispersion or a polydispersion. A mixture of monodispersed emulsions may be used. The grain size usually ranges from 0.1 to 2 μm, preferably from 0.2 to 1.5 μm. The silver halide grains can be of any crystal form, such as an octahedral form, a tetradecahedral form, and a tabular form having a high aspect ratio.

More specifically, any of the silver halide emulsions described in U.S. Pat. Nos. 4,500,626 (col. 50) and 4,628,021, RD 17029 (1978), and JP-A-62-253159 can be used in this invention.

The silver halide emulsion may be used in an untreated condition, but is usually used after chemical sensitization. Chemical sensitization of silver halide emulsion can be effected by known techniques, such as sulfur sensitization, reduction sensitization, noble metal sensitization, and combinations thereof. If desired, the chemical sensitization can be performed in the presence of a nitrogen-containing heterocyclic compound as disclosed in JP-A-62-253159.

The light-sensitive silver halide is usually coated to a coverage of from 1 mg to 10 g per m$^2$ in terms of the amount of silver.

The light-sensitive silver halide can be used in combination with an organic metal salt as an oxidizing agent. In this connection, organic silver salts are particularly preferred.

Organic compounds forming the organic silver salt oxidizing agents include benzotriazoles, fatty acids and others as disclosed in U.S. Pat. No. 4,500,626 (col. 52 to 53). Also useful are silver salts of carboxylic acids having an alkynyl group, e.g., silver phenylpropiolate, as disclosed in JP-A-60 113235 and silver acetylide as disclosed in JP-A-61-249044.

The organic silver salt preferably is used in an amount of from 0.01 to 10 mols, more preferably from 0.01 to 1 mol, per mole of the light-sensitive silver halide. The total silver coverage of the light-sensitive silver halide and the organic silver salt suitably ranges from 50 mg to 10 g/m².

The light-sensitive material of the invention can further contain various antifoggants or photographic stabilizers. Examples of these additives are azoles and azaindenes as described in RD 17643 (1978) (pp. 24 to 25), carboxylic acids and phosphoric acids containing nitrogen as described in JP-A-59 168442, mercapto compounds and metal salts thereof as described in JP-A-59-111636, and acetylene compounds as described in JP-A-62-87957.

The silver halide to be used may be spectrally sensitized with methine dyes or other sensitizing dyes. Usable sensitizing dyes include cyanine dyes, merocyanine dyes, complex cyanine dyes, complex merocyanine dyes, holopolar cyanine dyes, hemicyanine dyes, styryl dyes, and hemioxonol dyes. Specific examples of these dyes are described in U.S. Pat. No. 4,617,257, JP-A-59-180550 and JP-A-60-140335, and RD 17029 (1978) (pp. 12 to 13).

The sensitizing dyes may be used either individually or in combinations thereof. In particular, combinations of sensitizing dyes are frequently used for the purpose of supersensitization.

In addition to the sensitizing dyes, the emulsion can contain a dye having no spectral sensitizing activity by itself or a compound absorbing substantially no visible light but exhibiting supersensitizing activity, such as those disclosed in U.S. Pat. No. 3,615,641 and JP-A-63-23145.

The time for adding the sensitizing dyes to an emulsion can be during, before, or after chemical sensitization or, as proposed in U.S. Pat. Nos. 4,183,756 and 4,225,666, before or after nucleation of silver halide grains. The amount of the sensitizing dyes to be added usually ranges from $10^{-8}$ to $10^{-2}$ mol per mol of silver halide.

Binders which can be used in the layers constituting the light-sensitive material, and in a dye-fixing material which is often used in a diffusion transfer process, preferably include hydrophilic ones. Examples of hydrophilic binders are given in JP-A-62-253159 (pp. 26 to 28). In more detail, transparent or semi-transparent hydrophilic binders are preferred. Included therein are naturally-occurring compounds such as proteins, e.g., gelatin and gelatin derivatives; cellulose derivatives; and polysaccharides, e.g., starch, gum arabic, dextran and pullulan; and synthetic high polymers, e.g., polyvinyl alcohol, polyvinylpyrrolidone, and acrylamide polymers. Also usable are highly water-absorbing polymers described in JP A 62-245260, i.e., homopolymers of a vinyl monomer containing —COOM or —SO₃M (M is a hydrogen atom or an alkali metal) or copolymers of this vinyl monomer and other vinyl monomers (e.g., sodium methacrylate, ammonium methacrylate, or Sumika Gel L-5H produced by Sumitomo Chemical Co., Ltd.). These binders can be used either individually or in combinations of two or more thereof.

In cases where heat development is carried out with a trace amount of water being supplied, use of the above-mentioned highly water-absorbing polymer facilitates rapid absorption of water. Further, use of the highly water-absorbing polymer in a dye-fixing layer or a protective layer thereof prevents a transferred dye from re-transferring from the dye-fixing material to other materials.

The binder is preferably coated to a coverage of not more than 20 g, more preferably not more than 10 g, most preferably not more than 7 g, per m².

The layers constituting the light-sensitive material or dye-fixing material, inclusive of a backing layer, can contain various polymer latices for the purpose of improving film properties, for example, for dimensional stabilization, curl prevention, prevention of blocking, prevention of cracking, and prevention of pressure desensitization. For example, the polymer latices described in JP-A-62-245258, JP-A-62-136648, and JP-A-62-110066 can be employed. In particular, a polymer latex having a low glass transition point (40° C. or lower), when added to a mordanted layer, prevents the layer from cracking, and a polymer latex having a high glass transition point, when added to a backing layer, produces a curl prevention effect.

The light-sensitive material of the invention can contain a compound having a function of development activation combined with a function of image stabilization. Specific preferred examples of such a compound are described in U.S. Pat. No. 4,500,626 (col. 51 to 52).

In an image formation system according to dye diffusion transfer process, a light-sensitive material is used in combination with a dye-fixing material. The dye-fixing material and the light-sensitive material may be provided either on the same support or on separate supports. With respect to the relation between the light-sensitive material and the dye-fixing material, the relation to a support, and the relation to a white reflecting layer, the disclosure of U.S. Pat. No. 4,500,626 (col. 57) can be applied to the present invention.

The dye-fixing material which can be preferably used in the present invention comprises at least one layer containing a mordant and a binder. Any known mordant can be used in the present invention. Specific examples of the mordant are described in U.S. Pat. No. 4,500,626 (col. 58 to 59) and JP-A-61-88256 (pp. 32 to 47), JP-A-62-244043, and JP-A-62-244036. Dye-accepting high polymeric compounds as disclosed in U.S. Pat. No. 4,463,079 can also be used as a mordant.

If desired, the dye-fixing material may further contain auxiliary layers, such as a protective layer, a release layer, and an anti-curl layer. Provision of a protective layer is especially useful.

Layers constituting the light-sensitive material and dye-fixing material can contain a high-boiling organic solvent as a plasticizer, a slip agent, or an agent for improving release of the light-sensitive material from the dye-fixing material. Specific examples of usable high-boiling organic solvents are described in JP-A-62-253159 (p. 25) and JP-A-62-245253. The same purposes can also be achieved by using various kinds of silicone oil, inclusive of from dimethylsilicone oil to modified silicone oil obtained by introducing various organic groups to dimethylsiloxane. Particularly useful are the modified silicone oils of various kinds described in *Hensei Silicone Oil* (Modified Silicone Oil), pp. 6–18B, technical data published by Shin-Etsu Chemical Industry Co., Ltd., inter alia, carboxy-modified silicone X-22-3710 (tradename). The silicone oil described in JP-A-62-215953 and JP-A-63-46449 is also effective.

The light-sensitive material and dye-fixing material can further contain a discoloration inhibitor, such as an antioxidant, an ultraviolet absorbent, and a certain kind of metal complex.

The antioxidant includes chroman compounds, coumaran compounds, phenol compounds (e.g., hindered phenols), hydroquinone compounds, hindered amine compounds, and spiroindane compounds. The compounds described in JP-A-61-159644 are also effective.

The ultraviolet absorbents include benzotriazoles (e.g., those described in U.S. Pat. No. 3,533,794), 4-thiazolidone compounds (e.g., those described in U.S. Pat. No. 3,352,681), benzophenone compounds (e.g., those described in JP-A-46 2784), and the compounds described in JP-A-54-48535, JP-A-62-136641, and JP-A-61-88256. Ultraviolet absorbing polymers as described in JP-A-62-260152 are also effective.

The metal complexes include those described in U.S. Pat. Nos. 4,241,155, 4,245,018 (col. 3 to 36), and 4,254,195 (col. 3 to 8), JP-A-62-174741, JP-A-61-88256 (pp. 27 to 29), and JP-A-1-75568.

Examples of useful discoloration inhibitors are described in JP-A-62-215272 (pp. 125 to 137).

The discoloration inhibitor for preventing discoloration of the dye transferred into a dye-fixing material can be incorporated into the dye-fixing material beforehand or supplied to the dye-fixing material externally from, for example, the light-sensitive material.

The above-described antioxidants, ultraviolet absorbents and metal complexes may be used in combination thereof.

The light-sensitive material and dye-fixing material may contain a fluorescent brightening agent. It is particularly preferable that the fluorescent brightening agent is incorporated into the dye-fixing material or externally supplied thereto from the light-sensitive material, etc. Usable fluorescent brightening agents include the compounds described in K. Veenkataraman (ed.), *The Chemistry of Synthetic Dyes*, Vol. V, Ch. 8 and JP-A-61-143752. More specifically, the fluorescent brightening agents include stilbene compounds, coumarin compounds, biphenyl compounds, benzoxazolyl compounds, naphthalimide compounds, pyrazo line compounds, and carbostyril compounds. The fluorescent brightening agents may be used in combination with the discoloration inhibitors.

Hardening agents which can be used in layers constituting the light-sensitive material and dye-fixing material include those described in U.S. Pat. No. 4,678,739 (col. 41) and JP-A-59-116655, JP-A-62-245621, and JP-A-61-18942. Examples of the hardening agents are aldehyde compounds (e.g., formaldehyde), aziridine compounds, epoxy compounds

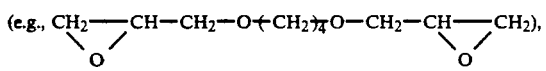

vinylsulfone compounds (e.g., N,N'-ethylenebis(vinylsulfonylacetamido)ethane), N-methylol compounds (e.g., dimethylolurea), and high polymeric compounds (e.g., those described in JP-A-62-234157).

For the purpose of improving coating properties, release properties and slip properties, antistatic charge prevention, and development acceleration, various types of surface active agents can be used in the layers constituting the light-sensitive material and dye-fixing material. Specific examples of the surface active agents are recited in JP-A-62-173463 and JP-A-62-183457.

For the purpose of improving slip properties, preventing antistatic charge, and improving release properties, organic fluorine compounds can also be added to the constituting layers. Typical examples of the organic fluorine compounds include fluorine-containing surface active agents as described in JP-B-57-9053 (col. 8 to 17) and JP-A-61-20944 and JP-A-62-135826, and hydrophobic fluorine compounds, such as oily fluorine compounds (e.g., fluorine oil) and solid fluorine-containing resins (e.g., tetrafluoroethylene resin).

Matting agents can be used in the light-sensitive material and dye-fixing material. The matting agents include those described in JP-A-61-88256 (p. 29), e.g., silicon dioxide, polyolefin, and polymethacrylate; and those described in JP-A 63-274944 and JP-A-63-274952, e.g., benzoguanamine resin beads, polycarbonate resin beads, and AS (acrylonitrile-styrene) resin beads.

Other additives which can be used in the light-sensitive material and dye-fixing material include thermal solvents, defoaming agents, antimicrobials, antifungals, and colloidal silica. Specific examples of these additives are described in JP-A-61-88256 (pp. 26 to 32).

In the present invention, an image formation accelerator can be used in the light-sensitive material and/or the dye-fixing material. The image formation accelerator serves functions of acceleration of an oxidation-reduction reaction between a silver salt oxidizing agent and a reducing agent; acceleration of dye formation, dye decomposition or release of a diffusing dye from a dye donating substance; acceleration of dye transfer from the light-sensitive material to the dye-fixing material; and the like. The formation accelerators are classified according to their physicochemical functions into bases or precursors thereof, nucleophilic compounds, high-boiling organic solvents (oils), thermal solvents, surface active agents, compounds exerting interaction on silver or silver ion, and the like. It should be understood that these groups of substances generally possess composite functions, and some of the above-described accelerating functions are exhibited by a single compound. For details, reference can be made to U.S. Pat. No. 4,678,739 (col. 38 to 40).

The base precursors include salts of organic acids and bases capable of decarboxylating on heat application and compounds capable of releasing an amine through intramolecular nucleophilic substitution, Lossen rearrangement or Beckmann rearrangement. Specific examples of the base precursors are described in U.S. Pat. No. 4,511,493 and JP-A-62-65038.

In a system wherein heat development and dye transfer are simultaneously carried out in the presence of a small amount of water, it is preferable for improving preservability of the light-sensitive material that the base and/or base precursor is incorporated into the dye-fixing material.

Further included in the base precursor are a combination of a sparingly soluble metal compound and a compound capable of forming a complex with the metallic ions constituting the sparingly soluble metal compound (called a complexing compound) as described in European Patent Publication 210,660 and compounds capable of forming a base by electrolysis as described in JP A-61-232451. The former type of base precursor system is particularly effective. The sparingly soluble metal compound and the complexing compound are advantageously incorporated separately into the light sensitive material and the dye-fixing material.

In order to always obtain a constant image irrespective of variations of developing temperature or time, the light-sensitive material and/or dye-fixing material can contain various kinds of development stopping agents.

The development stopping agent which can be used in the practice of the present invention includes compounds which rapidly neutralize or react with a base after proper development is reached to thereby reduce the base concentration in the film, and compounds which mutually act on silver and silver salts to inhibit development. Examples included therein are acid precursors capable of releasing an acid by heating, electrophilic compounds undergoing substitution reaction with a coexisting base by heating, nitrogen-containing heterocyclic compounds, mercapto compounds and precursors thereof. For details thereof, reference can be made in JP-A-62-253159 (pp. 31 to 32).

The support which can be used in the light-sensitive material or dye-fixing material should withstand the processing temperature employed and generally includes paper and plastic films. Examples of the support are polyethylene terephthalate films, polycarbonate films, polyvinyl chloride films, polystyrene films, polypropylene films, polyimide films, cellulose films (e.g., triacetyl cellulose films), and these films further containing pigments, e.g., titanium oxide; synthetic paper obtained from polypropylene, etc.; mixed paper obtained from a synthetic resin pulp (e.g., polyethylene) and a natural pulp; Yankee paper, baryta paper, coated paper (especially cast coated paper), metals, fabrics, glass, and so on. These supports can be used either alone or as a laminate with a synthetic high polymer film (e.g., polyethylene) on one or both sides thereof. In addition, the supports described in JP-A-62-253159 (pp. 29 to 31) can also be used.

In desired, the surface of the support may be coated with a hydrophilic binder having dispersed therein an antistatic agent such as semi-conducting metal oxides (e.g., alumina sol and tin oxide) and carbon black.

In carrying out image recording on the light-sensitive materials of the present invention, methods of imagewise exposure include direct photographing with cameras, etc. to obtain landscape or figure pictures; exposure through a reversal film or a negative film by use of a printer or an enlarger; scanning exposure of an original through a slit by use of an exposure apparatus of a copying machine; exposure to light emitted from a light-emitting diode (LED), laser, etc. by electrical signals of image information; and exposure to light emitted directly or via an optical system from an image display device, e.g., a CRT, a liquid crystal display, an electroluminescence display, a plasma display, etc.

The light source for image recording includes natural light, a tungsten lamp, an LED, a laser, and a CRT as described in U.S. Pat. No. 4,500,626 (col. 56).

Imagewise exposure can also be performed by use of a wavelength conversion element combining a nonlinear optical material and a coherent light source, e.g., a laser. The nonlinear optical material is a material which exhibits nonlinearity between polarization and an electrical field when exposed to an intense photo electrical field such as a laser ray, preferably including inorganic compounds, e.g., lithium niobate, potassium dihydrogenphosphate (KDP), lithium iodate, and $BaB_2O_4$; urea compounds, nitroaniline compounds, nitropyridine-N-oxide compounds, e.g., 3-methyl-4-nitropyridine-N-oxide (POM), and the compounds described in JP-A-61 53462 and JP-A-62-210432. Known wavelength conversion elements include a single-crystal light waveguide type, a fiber type, and the like, and any of them is useful.

The image information stated above includes image signals obtained from video cameras, electron still cameras, etc.; TV signals represented in Nippon Television Signal Code (NTSC); image signals obtained by dividing an original into numerous image elements by means of a scanner, etc.; and image signals prepared with a computer exemplified by CG (computer graphics) or CAD (computer aided drawing).

The light-sensitive material and/or dye-fixing material may contain a conductive heating element layer as a heating means for heat development or dye diffusion transfer. In this case, transparent or opaque heating elements described in JP-A-61-145544 can be used. The conductive layer also serves as an antistatic layer.

The temperature of development (and/or transfer) is set arbitrarily above about 10° C. In the case of heat development, which is preferably applied to the light-sensitive material of the present invention, the heating temperature is selected from about 50° C. to about 250° C., preferably from about 60° C. to about 180° C. Dye diffusion transfer may be effected either simultaneously with heat development or after completion of heat development. In the latter case, the heating temperature for dye diffusion transfer is set within a range of from room temperature up to the temperature employed for heat development, preferably of from 50° C. to a temperature lower than the heat development temperature by about 10° C.

Transfer of the dye takes place on heat application only, but may be accelerated by using a solvent.

As explained in JP-A-59-218443 and JP-A-61-238056, it is also advantageous to carry out development and transfer either simultaneously or successively by heating in the presence of a small amount of a solvent, especially water. According to this system, the heating temperature is preferably set within a range of from 50° C. to the boiling point of the solvent used. That is, in using water as a solvent, for example, a temperature is desirably set within a range of from 50° to 100° C.

Examples of the solvent to be used for acceleration of development and/or transfer of the diffusing dye to a dye fixing layer include water and a basic aqueous solution containing an inorganic alkali metal salt or an organic base (the bases enumerated with respect to the image formation accelerator can be used). A low-boiling solvent or a mixed solution of a low-boiling solvent and water or a basic aqueous solution can also be used. If desired, the solvent may contain a surface active agent, an antifoggant, or a combination of a sparingly soluble metal salt and a complexing compound.

The solvent can be supplied to either one or both of the dye-fixing material and light-sensitive material. The solvent is used in such a small amount as not more than the weight corresponding to the maximum swollen volume of the total coat, particularly not more than the remainder obtained by subtracting the weight of the total coat from the weight of the solvent corresponding to the maximum swollen volume of the total coat.

The solvent can be supplied to the light-sensitive layer or dye-fixing layer by, for example, the method of JP-A-61-147244 (p. 26). It is also possible to incorporate the solvent in either one or both of the light-sensitive material and dye-fixing material in the form of microcapsules.

In order to accelerate dye transfer, a hydrophilic thermal solvent that is solid at room temperature and melted at high temperatures may be incorporated into the light sensitive material or dye-fixing material. The hydrophilic thermal solvent may be incorporated in either one or both of the light-sensitive material and dye-fixing material. For example, it is incorporated into any of an emulsion layer, an intermediate layer, a protective layer, and a dye-fixing layer, preferably a dye-fixing layer and/or a layer adjacent thereto.

The hydrophilic thermal solvent to be used includes ureas, pyridines, amides, sulfonamides, imides, alcohols, oximes, and other heterocyclic compounds.

For the purpose of accelerating dye transfer, a high-boiling organic solvent may be added to the light-sensitive material and/or dye-fixing material.

Heating for development and/or transfer can be conducted by contact with a heated block or plate, a hot plate, a hot presser, a hot roller, a halogen lamp heater, an infrared lamp heater, or a far infrared lamp heater, or by passing through a high temperature atmosphere.

In cases where the light sensitive material and the dye-fixing material are brought into intimate contact, the method or condition of pressure application described in JP-A-61-147244 (p. 27) can be used.

Processing of the photographic element of the present invention can be carried out by means of any known heat development apparatus, such as those illustrated in JP-A-59-75247, JP-A-59-177547, JP-A-59-181353 and JP-A-60-18951 and JP-A-U-62-25944 (the term "JP-A-U" as used herein means an "unexamined published Japanese utility model application").

The color light-sensitive material of the present invention may be so designed as to be processed by a so-called wet color diffusion transfer process. In this case, all the foregoing description in connection with the light sensitive material and dye-fixing material, except for the additives inherent to heat development (e.g., organic silver salts}, can be applied. The base or electron transport agent may be supplied from a processing solution placed in a destroyable container. As is well known, this processing solution can contain a viscosity-imparting agent, etc. The wet color diffusion transfer process is well known in the art, and any of the known techniques and means therefor is applicable to the present invention.

The present invention is now illustrated in greater detail by way of the following Examples, but it should be understood that the present invention is not construed as being limited thereto. In these examples, all the percents are by weight unless otherwise specified.

EXAMPLE 1

Preparation of Emulsion (I)

In 100 ml of water were dissolved 20 g of gelatin and 3 g of sodium chloride, and the solution was kept at 75° C. while stirring well. To the gelatin aqueous solution were added 600 ml of an aqueous solution containing sodium chloride and potassium bromide and 600 ml of an aqueous silver nitrate solution containing 0.59 mol of silver nitrate at equal feed rates over a period of 40 minutes. There was prepared a monodispersed cubic silver chlorobromide emulsion having a mean grain size of 0.35 μm (bromine content: 80 mol%). After washing with water and desalting, 5 mg of sodium thiosulfate and 20 mg of 4-hydroxy-6-methyl-1,3,3a,7-tetraazaindene were added thereto to effect chemical sensitization to obtain 600 g of an emulsion for a first layer. The resulting emulsion was designated as Emulsion (I) for the 1st layer.

Preparation of Emulsion (II)

To a gelatin aqueous solution consisting of 20 g of gelatin, 3 g of sodium chloride, and 100 ml of water kept at 75° C. while stirring well, were added 600 ml of an aqueous solution containing sodium chloride and potassium bromide, 600 ml of an aqueous silver nitrate solution containing 0.59 mol of silver nitrate, and a dye solution consisting of 160 ml of a dye of the formula shown below and 400 ml of methanol at equal feed rates over a period of 40 minutes. There was obtained a monodispersed cubic silver chlorobromide emulsion (bromine content: 80 mol%) having a mean grain size of 0.35 μm and having the dye adsorbed thereon. After washing with water and desalting, 5 mg of sodium thiosulfate and 20 mg of 4-hydroxy-6-methyl 1,3,3a,7-tetraazaindene were added thereto to effect chemical sensitization to obtain 600 g of an emulsion for a third layer. This emulsion was designated as Emulsion (II) for the 3rd layer.

Dye:

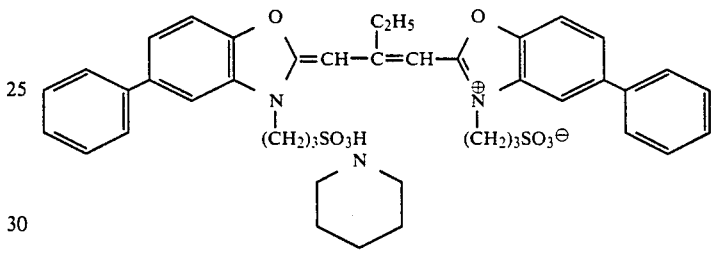

Preparation of Emulsion (III)

To a gelatin aqueous solution consisting of 20 g of gelatin, ammonium, and 100 ml of water kept at 50° C. while stirring well were added simultaneously 1000 ml of an aqueous solution containing potassium iodide and potassium bromide and 1,000 ml of an aqueous silver nitrate solution containing 1 mol of silver nitrate while keeping the pAg constant. There was obtained a monodispersed octahedral silver iodobromide emulsion having a mean grain size of 0.5 μm (iodine content: 5 mol %). After washing with water and desalting, 5 mg of chloroauric acid tetrahydrate and 2 mg of sodium thiosulfate were added to effect gold-sulfur sensitization at 60° C. to obtain 1 kg of an emulsion for a fifth layer. The resulting emulsion was designated as Emulsion (III) for the 5th layer.

Preparation of Gelatin Dispersion of Dye Donating Substance

In 46 ml of ethyl acetate were dissolved 18 g of a yellow dye donating substance (1)*, 9 g of an electron donor (1)*, and 9 g of tricyclohexyl phosphate at about 60° C to form a uniform solution. The resulting solution was mixed with 100 g of a 10% aqueous solution of lime-processed gelatin, 60 ml of water, and 1.5 g of sodium dodecylbenzenesulfonate by stirring, and the mixture was dispersed in a homogenizer at 10,000 rpm for 10 minutes. The resulting dispersion was designated as a yellow dye donating substance dispersion.

Magenta and cyan dye donating substance dispersions were prepared in the same manner as for the yellow dye donating substance dispersion, except for using a magenta dye donating substance (2)* or a cyan dye donating substance (3)*, respectively, in place of the yellow dye donating substance.

A light-sensitive material (sample 101) was prepared by using these emulsions and dispersions according to the following layer structure. The amounts shown are coated amounts

| 6th Layer (Protective Layer): | |
|---|---|
| Gelatin | 0.90 g/m² |
| Matting agent (silica) | 0.03 g/m² |
| Water-soluble polymer (1)* | 0.23 g/m² |
| Electron transport agent precursor (1)* | 0.08 g/m² |
| Surface active agent (1)* | 0.06 g/m² |
| Surface active agent (2)* | 0.13 g/m² |
| Hardening agent (1)* | 0.01 g/m² |
| ZnSO₂.7H₂O | 0.06 g/m² |
| 5th Layer (Blue Sensitive Layer): | |
| Emulsion (II) | 0.33 g of Ag/m² |
| Gelatin | 0.56 g/m² |
| Antifoggant (2)* | $5.5 \times 10^{-4}$ g/m² |
| Yellow dye donating substance (1)* | 0.40 g/m² |
| High-boiling organic solvent (1)* | 0.20 g/m² |
| Electron donor (1)* | 0.20 g/m² |
| Surface active agent (3)* | 0.05 g/m² |
| Zn(OH)₂ | 0.33 g/m² |
| Hardening agent (1)* | 0.01 g/m² |
| Water-soluble polymer (2)* | 0.02 g/m² |
| 4th Layer (Intermediate Layer): | |
| Gelatin | 0.70 g/m² |
| Zn(OH)2 | 0.31 g/m² |
| Reducing agent (1)* | 0.10 g/m² |
| Polymer (1)* | 0.05 g/m² |
| Surface active agent (5)* | $1.2 \times 10^{-3}$ g/m² |
| Surface active agent (1)* | 0.02 g/m² |
| Surface active agent (4)* | 0.07 g/m² |
| Electron transport agent precursor (1)* | 0.05 g/m² |
| Electron transport agent (1)* | 0.04 g/m² |
| Water-soluble polymer (2)* | 0.02 g/m² |
| Hardening agent (1)* | 0.01 g/m² |
| 3rd Layer (Green-Sensitive Layer): | |
| Emulsion (II) | 0.21 g of Ag/m² |
| Gelatin | 0.29 g/m² |
| Antifoggant (1)* | $6.0 \times 10^{-4}$ g/m² |
| Magenta dye donating substance (2)* | 0.31 g/m² |
| High-boiling organic solvent (1)* | 0.16 g/m² |
| Electron donor (1)* | 0.12 g/m² |
| Surface active agent (3)* | 0.04 g/m² |
| Electron transport agent (1)* | 0.04 g/m² |
| Hardening agent (1)* | 0.01 g/m² |
| Water-soluble polymer (2)* | 0.02 g/m² |
| 2nd Layer (Intermediate Layer): | |
| Gelatin | 0.80 g/m² |
| Zn(OH)₂ | 0.31 g/m² |
| Reducing agent (1)* | 0.10 g/m² |
| Polymer (1)* | 0.05 g/m² |
| Surface active agent (5)* | $1.2 \times 10^{-3}$ g/m² |
| Surface active agent (1)* | 0.06 g/m² |
| Surface active agent (4)* | 0.10 g/m² |
| Electron transport agent precursor (1)* | 0.05 g/m² |
| Water-soluble polymer (2)* | 0.03 g/m² |
| Hardening agent (1)* | 0.01 g/m² |
| 1st Layer (Red-Sensitive Layer): | |
| Emulsion (I) | 0.22 g of Ag/m² |
| Sensitizing dye (1)* | $6.7 \times 10^{-4}$ g/m² |
| Gelatin | 0.30 g/m² |
| Antifoggant (1)* | $6.1 \times 10^{-4}$ g/m² |
| Cyan dye donating substance (3)* | 0.28 g/m² |
| High-boiling organic solvent (1)* | 0.14 g/m² |
| Electron donor (1)* | 0.12 g/m² |
| Surface active agent (3)* | 0.04 g/m² |
| Electron transport agent (1)* | 0.04 g/m² |
| Hardening agent (1)* | 0.01 g/m² |
| Water-soluble polymer (2)* | 0.02 g/m² |
| Support: | |
| Polyethylene terephthalate (thickness: 100 μm) | |
| Backing Layer: | |
| Carbon black | 0.44 g/m² |
| Polyester | 0.30 g/m² |
| Polyvinyl chloride | 0.30 g/m² |

The additives used in the sample preparation are shown below.

Sensitizing dye (1)*

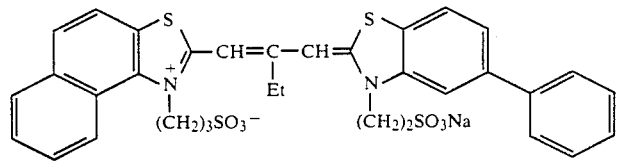

Water-soluble polymer (1)*:
Sumika Gel L-5(H) produced by Sumitomo Chemical Co., Ltd.

Water-soluble polymer (2)*:

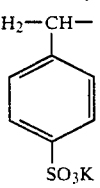

Surface active agent (1)*: Aerosol OT
Surface active agent (2)*:

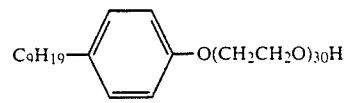

Surface active agent (3)*:

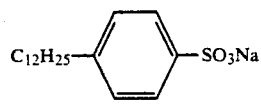
Surface active agent (4)*:
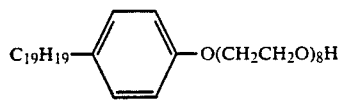
Surface active agent (5)*:
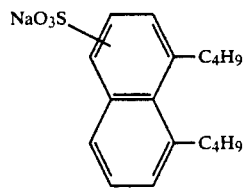
Hardening agent (1)*:
1,2-Bis(vinylsulfopnylacetamido)ethane
High-boiling organic solvent (1)*:
Tricyclohexyl phosphate
Antifoggant (1)*:
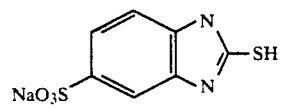
Antifoggant (2)*:
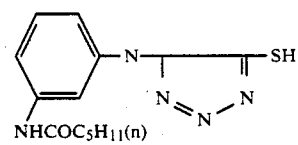
Reducing agent (1)*:
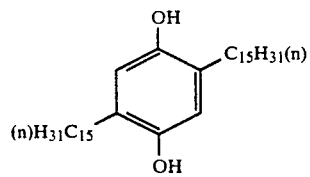
Polymer (1)*:
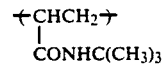
Electron donor (1)*:
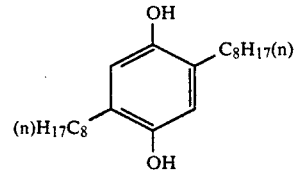
Electron transport agent precursor (1)*:

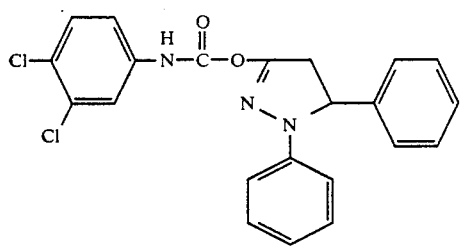

Electron transport agent (1)*:

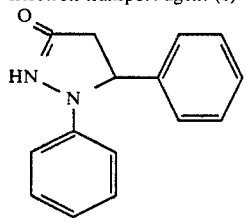

Yellow dye donating substance (1)*

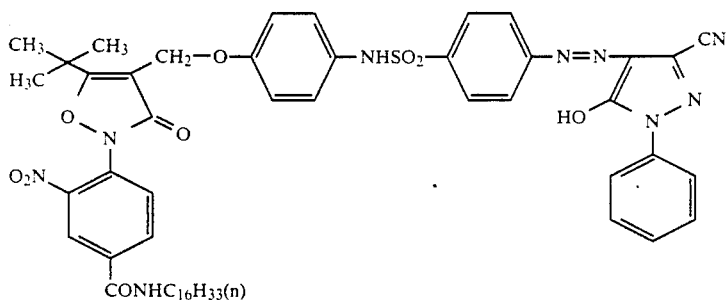

Magenta dye donating substance (2)*

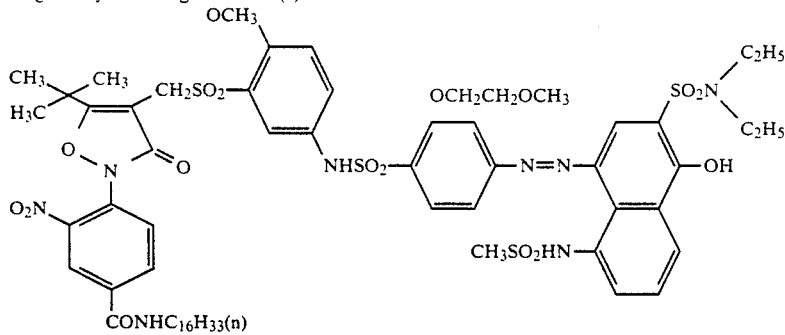

Cyan dye donating substance (3)*

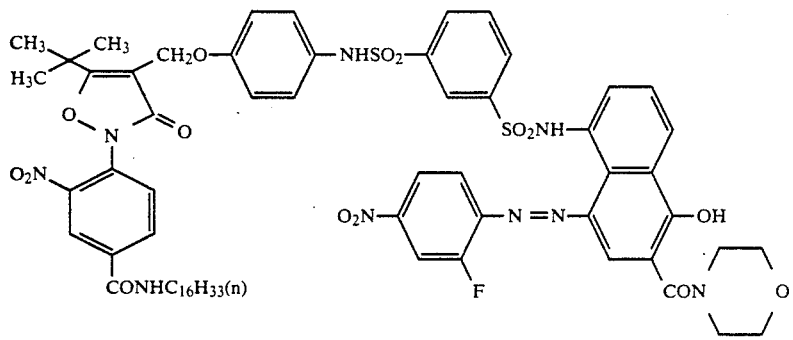

Light-sensitive materials (Samples 102 to 105) were prepared in the same manner as for Sample 101, except for replacing the electron donor (1)* in the 1st, 3rd, and 5th layers with a 0.7 time the molar amount of each of the compounds shown in Table 1.

Light-sensitive materials (Samples 112 to 115) were prepared in the same manner as for Sample 101, except for replacing the electron donor (1)* in the 1st, 3rd, and 5th layers with an equimolar amount of each of the compounds shown in Table 2.

In the preparation of samples, the reducing agent (1)* was incorporated into the 2nd and 4th layers in the form of a dispersion in the polymer (1)* prepared as follows. In 40 ml of ethyl acetate were dissolved 15 g of the reducing agent (1)* and 7.5 g of the polymer (1)* at about 60° C. to form a uniform solution. The resulting solution was mixed with 100 g of a 10% aqueous solution of lime-processed gelatin, and 3.8 ml of a 5% aqueous solution of the surface active agent (5)* while stirring, and the mixture was dispersed in a homogenizer at 10,000 rpm for 10 minutes.

Preparation of Dye-Fixing Material

A dye-fixing material (R-1) was prepared by coating the following layers on a polyethylene laminated paper support. The amounts shown are coated amounts.

| 3rd Layer: | |
|---|---|
| Gelatin | 0.05 g/m² |
| Silicone oil (1)** | 0.04 g/m² |
| Surface active agent (2)** | 0.001 g/m² |
| Surface active agent (3)** | 0.02 g/m² |
| Surface active agent (4)** | 0.10 g/m² |
| Guanidine picolinate | 0.45 g/m² |
| Polymer (5)** | 0.24 g/m² |
| 2nd Layer: | |
| Mordant (6)** | 2.35 g/m² |
| Polymer (7)** | 0.60 g/m² |
| Gelatin | 1.40 g/m² |
| Polymer (5)** | 0.21 g/m² |
| High-boiling solvent (8)** | 1.40 g/m² |
| Guanidine picolinate | 1.80 g/m² |
| Surface active agent (2)** | 0.02 g/m² |
| 1st Layer: | |
| Gelatin | 0.45 g/m² |
| Surface active agent (4)** | 0.01 g/m² |
| Polymer (5)** | 0.04 g/m² |
| Hardening agent (9)** | 0.30 g/m² |
| Support: | |
| Polyethylene-laminated paper support (thickness: 170 μm) | |
| 1st Backing Layer: | |
| Gelatin | 3.25 g/m² |
| Hardening agent (9)** | 0.25 g/m² |
| 2nd Backing Layer: | |
| Gelatin | 0.44 g/m² |
| Silicone oil (1)** | 0.08 g/m² |
| Surface active agent (2)** | 0.002 g/m² |
| Matting agent (10)** | 0.09 g/m² |

The additives used in the dye-fixing material (R-1) were as follows.

Silicone oil (1)**:

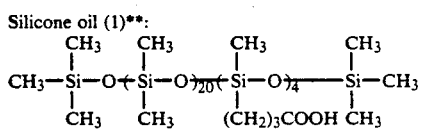

Surface active agent (2)**: Aerosol OT

Surface active agent (3)**:

$C_8F_{17}SO_2NCH_2COOK$
    |
    $C_3H_7$

Surface active agent (4)**:

$$C_{11}H_{23}CONHCH_2CH_2N^{\oplus}(CH_3)_2CH_2NOO^{\ominus}$$

Polymer (5)**:
Vinyl alcohol-sodium acrylate copolymer (75/25 by mole)

Polymer (7)**:
Dextran (molecular weight: 70,000)

Mordant (6)**:

$$-(CH_2-CH)_{\overline{60}}(CH_2-CH)_{\overline{30}}(CH_2-CH)_{\overline{10}}-$$
(with pyridine, pyrrolidone, and p-$SO_3K$ phenyl substituents)

High-boiling organic solvent (8)**:
Reofos 95 (produced by Ajinomoto Co., Inc.)

Hardening agent (9)**:

$$CH_2)_4(-O-CH_2-CH-\overset{O}{\overset{\diagup\diagdown}{\phantom{x}}}-CH_2)_2$$

Matting agent (10)**:
Benzoguanamine resin (average particle size: 10 μm)

Each of Samples 101 to 105 and 112 to 115 was exposed to light (500 lux) emitted from a tungsten lamp through a color decomposition filter (B, G, R or gray) having a continuous density gradation for 1 second.

Water was supplied on the emulsion surface of the exposed sample in an amount of 15 ml/m² by means of a wire bar, and the sample was then brought into contact with the dye-fixing material (R-1) in such a manner that the coat surfaces faced each other.

The light-sensitive material and the dye-fixing material were heated by passing through heat rollers set at such a temperature that the coat having absorbed water was heated to 85° C. for 15 second. Then, the light-sensitive material was peeled off the dye-fixing material. There was obtained a clear image of blue, green, red, or gray, respectively, on the dye fixing material.

The maximum density ($D_{max}$) and minimum density ($D_{min}$) of a cyan, magenta or yellow color of the gray portion were measured, and the results obtained are shown in Tables 1 and 2.

Further, the samples were preserved at 45° C. and 70% RH for 1 week and then tested in the same manner as described above. The results obtained are also shown in Tables 1 and 2.

TABLE 1

| Sample No. | Electron Donor | Immediately After Preparation | | | | | | After Preservation (45° C., 70% RH, 1 week) | | | | | |
|---|---|---|---|---|---|---|---|---|---|---|---|---|---|
| | | $D_{min}$ | | | $D_{max}$ | | | $D_{min}$ | | | $D_{max}$ | | |
| | | Yellow | Magenta | Cyan | Yellow | Magenta | Cyan | Yellow | Magenta | Cyan | Yellow | Magenta | Cyan |
| 101 | Electron donor (1)* | 0.18 | 0.18 | 0.14 | 2.0 | 2.2 | 2.2 | 0.45 | 0.42 | 0.36 | 2.0 | 2.2 | 2.1 |
| 102 | A-(3) | 0.17 | 0.16 | 0.14 | 2.0 | 2.1 | 2.1 | 0.20 | 0.19 | 0.19 | 2.1 | 2.2 | 2.0 |
| 103 | A-(5) | 0.18 | 0.18 | 0.13 | 2.1 | 2.2 | 2.2 | 0.21 | 0.21 | 0.18 | 2.1 | 2.2 | 2.2 |
| 104 | A-(17) | 0.17 | 0.16 | 0.13 | 2.0 | 2.1 | 2.1 | 0.20 | 0.21 | 0.18 | 2.1 | 2.1 | 2.1 |
| 105 | A-(26) | 0.16 | 0.17 | 0.14 | 2.0 | 2.2 | 2.2 | 0.19 | 0.21 | 0.20 | 2.0 | 2.0 | 2.1 |

TABLE 2

| Sample No. | Electron Donor | Immediately After Preparation ||||||  After Preservation (45° C., 70% RH, 1 week) ||||||
| | | $D_{min}$ ||| $D_{max}$ ||| $D_{min}$ ||| $D_{max}$ |||
| | | Yellow | Magenta | Cyan | Yellow | Magenta | Cyan | Yellow | Magenta | Cyan | Yellow | Magenta | Cyan |
|---|---|---|---|---|---|---|---|---|---|---|---|---|---|
| 101 | Electron donor (1)* | 0.18 | 0.18 | 0.14 | 2.0 | 2.2 | 2.2 | 0.45 | 0.42 | 0.36 | 2.0 | 2.2 | 2.1 |
| 112 | B-(6) | 0.15 | 0.16 | 0.14 | 2.0 | 2.1 | 2.1 | 0.18 | 0.19 | 0.17 | 2.0 | 2.1 | 2.1 |
| 113 | B-(10) | 0.15 | 0.18 | 0.15 | 2.1 | 2.1 | 2.2 | 0.17 | 0.20 | 0.17 | 2.1 | 2.1 | 2.1 |
| 114 | B-(17) | 0.16 | 0.17 | 0.14 | 2.1 | 2.1 | 2.2 | 0.18 | 0.20 | 0.16 | 2.1 | 2.1 | 2.2 |
| 115 | B-(30) | 0.15 | 0.18 | 0.15 | 2.0 | 2.0 | 2.1 | 0.18 | 0.20 | 0.18 | 2.0 | 2.0 | 2.1 |

As is apparent from Tables 1 and 2, it was proved that the light-sensitive materials containing the reducing agent (electron donor) according to the present invention provide an image having a high density and low stain and exhibit improved preservability.

EXAMPLE 2

Light-sensitive materials (Samples 201 to 205 and 212 to 215) were prepared in the same manner as for Samples 101 to 105 and 112 to 115 of Example 1, except for excluding the reducing agent (1)*, polymer (1)* and surface active agent (5)* from the 2nd and 4th layers (intermediate layers).

Light-sensitive materials (Samples 301 to 305 and 312 to 315) were prepared in the same manner as for Samples 201 to 205 and 212 to 215, except that each of the 2nd and 4th intermediate layers further contained a dispersion of the same electron donor as used in the 1st, 3rd, and 5th layers in an amount equimolar to the reducing agent (1)* of Sample 101.

The dispersion of the electron donor was prepared as follows. In 40 ml of ethyl acetate were dissolved 28 mmol of the electron donor and 6 g of the high-boiling organic solvent (1) at about 60° C. to prepare a uniform solution. The solution was mixed with 100 g of a 10% aqueous solution of lime-processed gelatin and 13.5 ml of a 5% aqueous solution of the surface active agent (3)* by stirring, and the mixture was dispersed in a homogenizer at 10,000 rpm for 10 minutes.

Each of Samples 201 to 205, 212 to 215, 301 to 305, and 312 to 315 was exposed to light through a continuous wedge whose density gradation was perpendicular to the light wave direction by the use of a spectrograph and then development processed using the dye-fixing material (R-1) in the same manner as described in Example 1. As a result, Samples 201 to 205 and 212 to 215 were found to be insufficient in color reproducibility, while Samples 301 to 305, and 312 to 315 all proved satisfactory in color reproduction.

Further, Samples 201 to 205, 212 to 215, 301 to 305, and 312 to 315 were preserved at 45° C. and 70% RH for 1 week, and the photographic characteristics of these samples were compared with those of the samples immediately after the preparation. As a result, Samples 201 and 301 showed a great increase of $D_{min}$, while the other samples proved free from variations of photographic characteristics.

It can be seen accordingly that use of the reducing agent (electron donor) of the present invention in intermediate layers further improve color reproducibility and preservability.

EXAMPLE 3

A multilayer color light sensitive material (Sample 401) was prepared by using the same emulsions, dye donating substances, electron donor, and electron transport agent as used in Sample 101 according to the following layer structure. Other additives were the same as those used in Sample 101 unless otherwise specified.

The organic silver salt emulsion used in the 1st, 3rd and 5th layers of Sample 401 was prepared as follows. Twenty grams of gelatin and 5.9 g of 4-acetylaminophenylpropiolic acid were dissolved in 1000 ml of a 0.1% aqueous solution of sodium hydroxide and 200 ml of ethanol, and the solution was kept at 40° C. under stirring. To the solution was added a solution of 4.5 g of silver nitrate in 200 ml of water over a period of 5 minutes. Any excess salt was removed by a sedimentation method. The dispersion was then adjusted to a pH of 6.3 to obtain 300 g of an organic silver salt dispersion.

The antifoggant precursor (1)* in the 1st, 3rd and 5th layers was used in an amount of 0.2 mol per mol of the dye donating substance in the form of an oil dispersion together with the dye donating substance and electron donor as prepared in the same manner as in Example 1. The amounts shown below are coated amounts.

| 6th Layer (Protective Layer): | |
|---|---|
| Gelatin | 0.91 g/m² |
| Matting agent (silica) | 0.03 g/m² |
| Surface active agent (1)* | 0.06 g/m² |
| Surface active agent (2)* | 0.13 g/m² |
| Hardening agent (1)* | 0.01 g/m² |
| Base precursor (1)* | 0.30 g/m² |
| 5th Layer (Blue-Sensitive Layer): | |
| Emulsion (III) | 0.30 g of Ag/m² |
| Organic silver salt emulsion | 0.25 g of Ag/m² |
| Gelatin | 1.00 g/m² |
| Antifoggant precursor (1)* | 0.07 g/m² |
| Yellow dye donating substance (1)* | 0.50 g/m² |
| High-boiling organic solvent (1)* | 0.75 g/m² |
| Electron donor (1)* | 0.35 g/m² |
| Surface active agent (3)* | 0.05 g/m² |
| Electron transport agent (1)* | 0.04 g/m² |
| Electron transport agent precursor (1)* | 0.08 g/m² |
| Thermal solvent (1)* | 0.02 g/m² |
| Hardening agent (1)* | 0.01 g/m² |
| Base precursor (1)* | 0.27 g/m² |
| Water-soluble polymer (2)* | 0.02 g/m² |
| 4th Layer (Intermediate Layer): | |
| Gelatin | 0.75 g/m² |
| Reducing agent (1)* | 0.24 g/m² |
| High-boiling organic solvent (1)* | 0.12 g/m² |
| Surface active agent (1)* | 0.02 g/m² |
| Surface active agent (4)* | 0.07 g/m² |
| Water-soluble polymer (2)* | 0.02 g/m² |
| Hardening agent (1)* | 0.01 g/m² |
| Base precursor (1)* | 0.25 g/m² |
| 3rd Layer (Green-Sensitive Layer): | |
| Emulsion (II) | 0.20 g of Ag/m² |
| Organic silver salt emulsion | 0.20 g of Ag/m² |
| Gelation | 0.85 g/m² |
| Antifoggant precursor (1)* | 0.04 g/m² |
| Magenta dye donating substance (2) | 0.37 g/m² |
| High-boiling organic solvent (1)* | 0.55 g/m² |
| Electron donor (1)* | 0.20 g/m² |
| Surface active agent (3)* | 0.04 g/m² |
| Electron transport agent (1)* | 0.04 g/m² |
| Electron transport agent precursor (1)* | 0.08 g/m² |
| Thermal solvent (1)* | 0.16 g/m² |

| -continued | |
|---|---|
| Hardening agent (1)* | 0.01 g/m² |
| Base precursor (1)* | 0.25 g/m² |
| Water-soluble polymer (2)* | 0.02 g/m² |
| 2nd Layer (Intermediate Layer): | |
| Gelatin | 0.80 g/m² |
| Reducing agent (1)* | 0.24 g/m² |
| High-boiling organic solvent (1)* | 0.12 g/m² |
| Surface active agent (1)* | 0.06 g/m² |
| Surface active agent (4)* | 0.10 g/m² |
| Water-soluble polymer (2)* | 0.03 g/m² |
| Base precursor (1)* | 0.25 g/m² |
| Hardening agent (1)* | 0.01 g/m² |
| 1st Layer (Red-Sensitive Layer): | |
| Emulsion (I) | 0.20 g of Ag/m² |
| Organic silver salt emulsion | 0.20 g of Ag/m² |
| Sensitizing dye (1)* | $1.07 \times 10^{-3}$ g/m² |
| Gelatin | 0.85 g/m² |
| Antifoggant precursor (1)* | 0.04 g/m² |
| Thermal solvent (1)* | 0.16 g/m² |
| Base precursor (1)* | 0.16 g/m² |
| Cyan dye donating substance (3)* | 0.40 g/m² |
| High-boiling organic solvent (1)* | 0.60 g/m² |
| Electron donor (1)* | 0.20 g/m² |
| Surface active agent (3)* | 0.04 g/m² |
| Electron transport agent (1)* | 0.04 g/m² |
| Electron transport agent precursor (1)* | 0.08 g/m² |
| Hardening agent (1)* | 0.01 g/m² |
| Water-soluble polymer (2)* | 0.02 g/m² |
| Support: | |
| Polyethylene terephthalate (thickness: 100 μm) | |
| Backing Layer: | |
| Carbon black | 0.44 g/m² |
| Polyester | 0.30 g/m² |
| Polyvinyl chloride | 0.30 g/m² |

Antifoggant precursor (1)*:

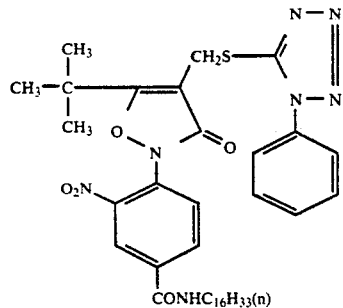

Thermal solvent (1)*: benzenesulfonamide
Base precursor (1)*: guanidine 4-chlorophenylsulfonylacetate Sample 402 and 403 were prepared in the same manner as for Sample 401, except for replacing the electron donor (1)* used in the 1st, 3rd and 5th layers with an equimolar amount of Compound A-(5) or A-(24) according to the present invention.

Samples 412 and 413 were prepared in the same manner as for Sample 401, except for replacing the electron donor (1)* used in the 1st, 3rd and 5th layers with Compound B-(6) or B-(23) according to the present invention.

Preparation of Dye-fixing Material (R-2)

In 200 ml of water was dissolved 10 g of poly(methyl acrylate-co-N,N,N-trimethyl-N-vinylbenzylammonium chloride) (methyl acrylate:vinylbenzylammonium chloride=1:1), and the solution was uniformly mixed with 100 g of a 10% aqueous solution of lime-processed gelatin. To the mixture was added the hardening agent, and the resulting coating composition was uniformly coated on a paper support laminated with polyethylene having dispersed therein titanium dioxide to a wet thickness of 90 μm, followed by drying to prepare a dye-fixing material (R-2) having a mordanted layer.

Each of Samples 401 to 403 and 412 to 413 was exposed to light in the same manner as in Example 1 and uniformly heated on a heat block heated at 140° C. for 30 seconds.

Water was supplied to the coat surface of the dye-fixing material (R-2) in an amount of 20 ml/m², and then brought into contact with the heat-treated light-sensitive material in such a manner that the coat surfaces faced each other.

Thereafter, the light-sensitive material and the dye-fixing material were passed through a laminator heated at 80° C. at a linear speed of 12 mm/sec, and the light-sensitive material was peeled off the dye-fixing material. There was obtained a positive image on the dye-fixing material.

The maximum densities ($D_{max}$) of cyan, magenta and yellow colors of the gray portion were measured. Further, after being preserved at 45° C. and 70% RH for 1 week, each of the samples was processed in the same manner as described above, and the photographic characteristics were compared with those of the samples immediately after the preparation. As a result, Sample 401 showed a great increase of $D_{min}$ due to the accelerated aging, while the variations of the photographic characteristics proved small in Samples 402, 403, 412 and 413. It can thus been seen that preservability of the light-sensitive materials can be improved by using the reducing agent (electron donor) of the present invention.

EXAMPLE 4

A transparent polyethylene terephthalate support was coated with the following layers successively in the order listed to prepare a light-sensitive material (Sample 501). The additives used were the same as those used in Sample 101 unless otherwise specified. The amounts shown are coated amounts.

| | |
|---|---|
| (I) Dye-receiving layer containing: | |
| (a) Copoly[styrene-N vinylbenzyl-N,N,N-trihexylammonium chloride] | 4.0 g/m² |
| (b) Gelatin | 4.0 g/m² |
| (c) Surface active agent (2)* | 0.2 g/m² |
| (II) White reflecting layer containing: | |
| (a) Titanium dioxide | 22 g/m² |
| (b) Gelatin | 2.2 g/m² |
| (c) Surface active agent (2)* | 0.2 g/m² |
| (III) Opaque layer containing: | |
| (a) Carbon black | 2.7 g/m² |
| (b) Gelatin | 2.7 g/m² |
| (c) Surface active agent (2)* | 0.2 g/m² |
| (IV) Cyan dye donating layer containing: | |
| (a) Gelatin dispersion containing 0.33 mmol/m² of the cyan dye donating substance (3)*, 0.4 mmol/m² of the electron donor (1)*, and 200 mg/m² of the high-boiling organic solvent (1)* | |
| (d) Gelatin (inclusive of the gelatin in (a) above) | 1.1 g/m² |
| (c) Surface active agent (1)* | 0.20 g/m² |
| (V) Red-sensitive layer containing: | |
| (a) Emulsion (I) | 0.5 g of Ag/m² |
| (b) Sensitizing dye (1)* | $1.3 \times 10^{-3}$ g/m² |
| (c) Gelatin (inclusive of the gelatin in (a) above) | 1.1 g/m² |
| (c) Surface active agent (1)* | 0.2 g/m² |
| (VI) Intermediate layer containing: | |
| (a) 2,5-Di(t-pentadecyl)hydroquinone | 0.82 g/m² |
| (b) Vinyl acetate | 0.8 g/m² |
| (c) Gelatin | 0.4 g/m² |
| (d) Surface active agent (1)* | 0.2 g/m² |
| (VII) Magenta dye donating layer containing: | |
| (a) Gelatin dispersion containing 0.3 mmol/m² of the | |

-continued

| | |
|---|---|
| magenta dye donating substance (2)*, 0.4 mmol/m² of the electron donor (1)*, and 200 mg/m² of the high-boiling organic solvent (1)* | |
| (b) Gelatin (inclusive of the gelatin in (a) above) | 1.1 g/m² |
| (c) Surface active agent (1)* | 0.2 g/m² |
| (VIII) Green-sensitive layer containing: | |
| (a) Emulsion (II) | 0.5 g of Ag/m² |
| (b) Gelatin (inclusive of the gelatin in Emulsion (II) | 1.1 g/m² |
| (c) Surface active agent (1)* | 0.2 g/m² |
| (IX) Intermediate layer having the same composition as the layer (VI). | |
| (X) Yellow dye donating layer containing: | |
| (a) Gelatin dispersion containing 0.5 mmol/m² of the yellow dye donating substance (1)*, 0.6 mmol/m² of the electron donor (1)*, and 250 mg/m² of the high-boiling organic solvent (1)* | |
| (b) Gelatin (inclusive of the gelatin in (a)) | 1.1 g/m² |
| (c) Surface active agent (1)* | 0.2 g/m² |
| (XI) Blue-sensitive layer containing: | |
| (a) Emulsion (III) | 0.5 g of Ag/m² |
| (b) Gelatin (inclusive of the gelatin in Emulsion (III)) | 1.1 g/m² |
| (c) Surface active agent (1)* | 0.2 g/m² |
| (XII) Protective layer containing: | |
| (a) Polyethylene acrylate latex | 0.9 g/m² |
| (b) Tinuvin | 0.5 g/m² |
| (c) Triacryloyl perhydrotriazine (hardening agent) | 0.026 g/m² |
| (d) Gelatin | 1.3 g/m² |
| (e) Surface active agent (1)* | 0.2 g/m² |

Samples 502 and 512 were prepared in the same manner as for Sample 501, except for replacing the electron donor (1)* used in the (IV), (VII) and (X) layers with an equimolar amount of Compound A-(5) or (B-1), respectively.

Then, a transparent polyethylene terephthalate film was coated with the following layers successively in the order listed to prepare a cover sheet. The amounts shown are coated amounts.

| | |
|---|---|
| (I) Acid neutralizing layer containing: | |
| (a) Polyacrylic acid | 17 g/m² |
| (b) N-Hydroxysuccinimidebenzene-sulfonate | 0.06 g/m² |
| (c) Ethylene glycol | 0.5 g/m² |
| (II) Timing layer (thickness: 2 μm) comprising cellulose acetate: (acetyl value: 54%) | |
| (III) Timing layer thickness: 4 μm) comprising a vinylidene chloride/acrylic acid copolymer latex | |

A processing solution having the following composition was prepared.

| | |
|---|---|
| Potassium hydroxide | 48 g |
| 4-Hydroxymethyl-4-methyl-1-p-tolyl-3-pyrazolidone | 10 g |
| 5-Methylbenzotriazole | 1.5 g |
| Sodium sulfite | 1.5 g |
| Potassium bromide | 1 g |
| Benzyl alcohol | 1.5 ml |
| Carboxymethyl cellulose | 6.1 g |
| Carbon black | 150 g |
| Water to make | 1 liter |

Each of Samples 501, 502, and 512 was exposed to light through an optical wedge, brought into contact with the cover sheet, and passed through a pair of rollers to uniformly spread the processing solution therebetween to a thickness of 80 μm. One hour later, sensitometry was conducted. The results obtained are shown in Table 3.

TABLE 3

| Sample No. | Electron Donor | $D_{max}$ Yellow | $D_{max}$ Magenta | $D_{max}$ Cyan | $D_{min}$ Yellow | $D_{min}$ Magenta | $D_{min}$ Cyan |
|---|---|---|---|---|---|---|---|
| 501 | Electron donor (1)* | 2.1 | 2.2 | 2.2 | 0.18 | 0.21 | 0.20 |
| 502 | A-(5) | 2.0 | 2.0 | 2.1 | 0.18 | 0.18 | 0.20 |
| 512 | B-(1) | 2.1 | 2.2 | 2.1 | 0.17 | 0.18 | 0.20 |

Samples 501, 502, and 512 were preserved at 45° C. and 70% RH for 1 week and then processed in the same manner as described above. The photographic characteristics of the processed samples were compared with those of the samples immediately after the preparation. As a result, none of the samples underwent a substantial variation of $D_{max}$, but an increase of $D_{min}$ observed in Sample 501 was found to be greater than that in Samples 502 and 512. Accordingly, it can be seen that preservability of the light-sensitive material can be improved by using the reducing agent according to the present invention.

While the invention has been described in detail and with reference to specific embodiments thereof, it will be apparent to one skilled in the art that various changes and modifications can be made therein without departing from the spirit and scope thereof.

What is claimed is:

1. A color light-sensitive material comprising a support having provided thereon a light-sensitive silver halide, a binder, a reducible dye donating compound, and at least one reducing agent selected from the group consisting of a compound represented by formula (IA) and a compound represented by formula (IB):

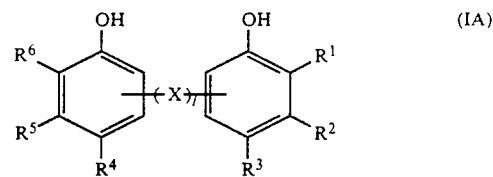

wherein $R^1$, $R^2$, $R^3$, $R^4$, $R^5$, and $R^6$, which may be the same or different, each represents a hydrogen atom, a halogen atom, a hydroxyl group, a substituted or unsubstituted alkyl group, a substituted or unsubstituted aryl group, a substituted or unsubstituted acylamino group, a substituted or unsubstituted alkoxy group, a substituted or unsubstituted aryloxy group, a substituted or unsubstituted alkylthio group, a substituted or unsubstituted arylthio group, a substituted or unsubstituted acyl group, a substituted or unsubstituted sulfonyl group, a substituted or unsubstituted carbamoyl group, or a substituted or unsubstituted sulfamoyl group, provided that at least one of $R^1$ and $R^3$ and at least one of $R^4$ and $R^6$ represent a hydroxyl group; or any adjacent two of $R^1$, $R^2$, $R^3$, $R^4$, $R^5$, and $R^6$ are connected to each other to form a carbocyclic ring; X represents a divalent linking group; and l represents 0 or 1;

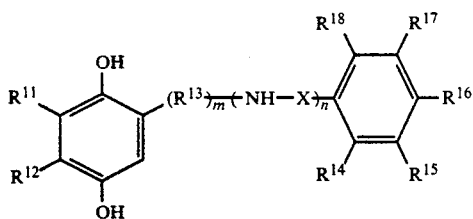

(IB)

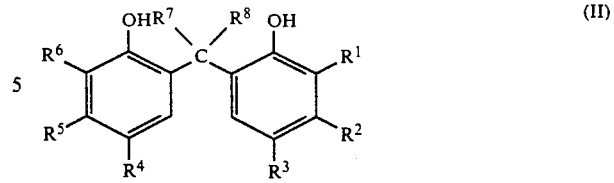

(II)

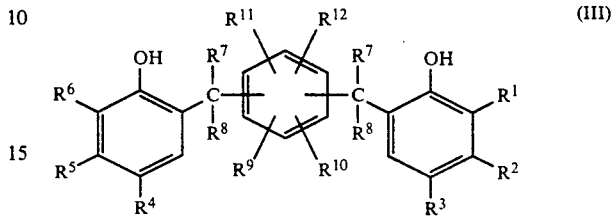

(III)

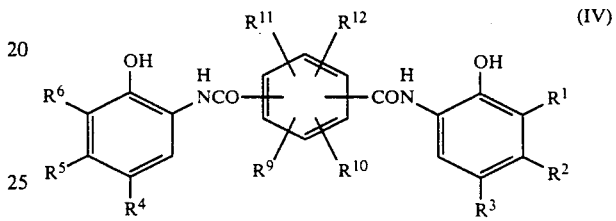

(IV)

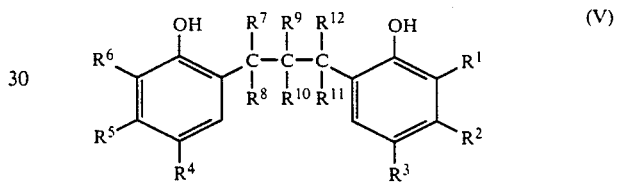

(V)

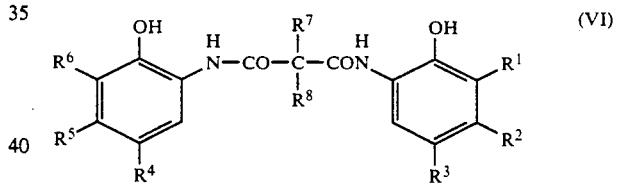

(VI)

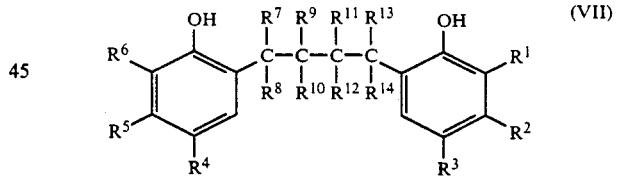

(VII)

wherein $R^{11}$ and $R^{12}$, which may be the same or different, each represents a hydrogen atom, a halogen atom, a substituted or unsubstituted alkyl group, a substituted or unsubstituted aryl group, a substituted or unsubstituted acylamino group, a substituted or unsubstituted alkoxy group, a substituted or unsubstituted aryloxy group, a substituted or unsubstituted alkylthio group, a substituted or unsubstituted arylthio group, a substituted or unsubstituted acyl group, a substituted or unsubstituted sulfonyl group, a substituted or unsubstituted carbamoyl group, or a substituted or unsubstituted sulfamoyl group, or $R^{11}$ and $R^{12}$ are taken together to form a carbocyclic ring; $R^{13}$ represents an unsubstituted or alkyl-substituted alkylene group: $R^{14}$, $R^{15}$, $R^{16}$, $R^{17}$, and $R^{18}$, which may be the same or different, each represents a hydrogen atom, a halogen atom, a cyano group, a nitro group, a substituted or unsubstituted alkyl group, a substituted or unsubstituted acylamino group, a substituted or unsubstituted sulfonamido group, a substituted or unsubstituted alkoxy group, a substituted or unsubstituted aryloxy group, a substituted or unsubstituted alkylthio group, a substituted or unsubstituted arylthio group, a substituted or unsubstituted amino group, a substituted or unsubstituted acyl group, a substituted or unsubstituted acyloxy group, a substituted or unsubstituted carbamoyl group, a substituted or unsubstituted carbamoylamino group, a substituted or unsubstituted sulfamoyl group, a substituted or unsubstituted sulfamoylamino group, a substituted or unsubstituted alkoxycarbonyl group, a substituted or unsubstituted aryloxycarbonyl group, a substituted or unsubstituted heterocyclic group, a substituted or unsubstituted alkoxysulfonyl group, or a substituted or unsubstituted aryloxysulfonyl group; $R^{14}$, $R^{15}$, and $R^{16}$ each may further represent a hydroxyl group; or any adjacent two of $R^{14}$, $R^{15}$, $R^{16}$, $R^{17}$, and $R^{18}$ are connected to each other to form a carbocyclic or heterocyclic ring; X represents —CO— or —SO$_2$—; m represents 1 and n represents 0 or 1; and the total number of carbon atoms in $R^{11}$, $R^{12}$, $R^{13}$, $R^{14}$, $R^{15}$, $R^{16}$, $R^{17}$, and $R^{18}$ is 8 or more.

2. A color light sensitive material as claimed in claim 1, wherein $R^1$ and $R^6$ each represents a hydroxyl group, and $R^3$ and $R^4$ each represents an atom or a group other than a hydroxyl group.

3. A color light-sensitive material as claimed in claim 1, wherein the total number of the carbon atoms in $R^1$, $R^2$, $R^3$, $R^4$, $R^5$, $R^6$, and X is 10 or more.

4. A color light-sensitive material as claimed in claim 1, wherein the compound represented by formula (IA) is represented by formulae (II), (III), (IV), (V), (VI) or (VII):

wherein $R^1$, $R^2$, $R^3$, $R^4$, $R^5$, and $R^6$ each represents a hydrogen, atom, a halogen atom, a hydroxyl group, a substituted or unsubstituted alkyl group, a substituted or unsubstituted aryl group, a substituted or unsubstituted acylamino group, a substituted or unsubstituted alkoxy group, a substituted or unsubstituted aryloxy group, a substituted or unsubstituted alkylthio group, a substituted or unsubstituted arylthio group, a substituted or unsubstituted acyl group, a substituted or unsubstituted sulfonyl group, a substituted or unsubstituted carbamoyl group, or a substituted or unsubstituted sulfamoyl group, provided that at least one of $R^1$ and $R^3$ and at least one of $R^4$ and $R^6$ represent a hydroxyl group; or any adjacent two of $R^1$, $R^2$, $R^3$, $R^4$, $R^5$, and $R^6$ are connected to each other to form a Carbocyclic ring; and $R^7$, $R^8$, $R^9$, $R^{10}$, $R^{11}$, $R^{12}$, $R^{13}$, and $R^{14}$, which may be the same or different, each represents a hydrogen atom, a nitro group, a halogen atom, substituted or unsubstituted alkyl, aryl, acylamino, alkoxyl, aryloxy, alkylthio, arylthio, acyl, sulfonyl, carbamoyl or sulfamoyl group, or a substituted or unsubstituted amino, sulfonamido, acyloxy, alkoxycarbonyl, aryloxycarbonyl, alkoxycarbonyloxy, aryloxycarbonyloxy, alkoxysulfonyl, aryloxysulfonyl, heterocyclic, carbamoylamino or sulfamoylamino group; or $R^7$ and $R^8$ are taken together to form a 5- to 20-membered carbocyclic ring.

5. A color light-sensitive material as claimed in claim 1, Wherein $R^{11}$ and $R^{12}$ each represents a hydrogen atom, a halogen atom, or a substituted or unsubstituted alkyl, alkoxy or alkylthio group.

6. A color light-sensitive material as claimed in claim 1, wherein $R^{13}$ contains not more than 3 carbon atoms.

7. A color light-sensitive material as claimed in claim 1, wherein $R^{14}$, $R^{15}$, $R^{16}$, $R^{17}$, and $R^{18}$ each represents a hydrogen atom or a substituted or unsubstituted alkyl, acylamino, sulfonamido, alkoxy, acyloxy, carbamoyl, sulfamoyl, alkoxycarbonyl or alkoxysulfonyl group.

8. A color light-sensitive material as claimed in claim 1, wherein said reducing agent is present in an amount of from 0.001 to 20 mols per mol of silver.

9. A color light-sensitive material as claimed in claim 1, wherein said reducing agent is present in an amount of from 0.05 to 10 mols per mol of the reducible dye donating substance.

* * * * *